United States Patent [19]

Jewell

[11] Patent Number: 5,747,311
[45] Date of Patent: May 5, 1998

US005747311A

[54] PROCESS FOR CHEMICAL MODIFICATION OF REACTANTS BY MICROBES

[75] Inventor: William J. Jewell, Ithaca, N.Y.

[73] Assignee: Microgen Corporation, Ithaca, N.Y.

[21] Appl. No.: 517,276

[22] Filed: Aug. 22, 1995

[51] Int. Cl.[6] ............ C12N 11/00; C12N 11/14; C02F 3/00; C02F 3/02
[52] U.S. Cl. ............ 435/176; 435/174; 435/180; 210/600; 210/601; 210/620; 210/630
[58] Field of Search ............ 210/600, 601, 210/611, 612, 613, 615, 616, 617, 618, 619, 620–630; 435/168, 177, 180, 182, 174, 176

[56] References Cited

U.S. PATENT DOCUMENTS

| | | | |
|---|---|---|---|
| 4,009,099 | 2/1977 | Jeris | 210/612 |
| 4,182,675 | 1/1980 | Jeris | 210/612 |
| 4,413,058 | 11/1983 | Arcuri et al. | 435/161 |
| 4,415,454 | 11/1983 | Fuchs | 210/616 |
| 4,454,038 | 6/1984 | Shimodaira et al. | 210/150 |
| 4,566,971 | 1/1986 | Reimann et al. | 210/616 |
| 4,620,931 | 11/1986 | Hirata et al. | 210/617 |
| 4,843,105 | 6/1989 | Reischl et al. | 521/54 |
| 5,217,616 | 6/1993 | Sanyal et al. | 210/617 |
| 5,486,292 | 1/1996 | Bair et al. | 210/616 |

*Primary Examiner*—Leon B. Lankford, Jr.
*Assistant Examiner*—Christopher Tate
*Attorney, Agent, or Firm*—Nixon, Hargrave, Devans & Doyle LLP

[57] ABSTRACT

The present invention relates to a method for chemically modifying a reactant using microbes. The method includes providing a particulate material which includes a plastic carrier and microbes attached to the carrier. The particulate material is dispersed in a dispersing fluid and has a specific gravity less than that of the dispersing fluid. When the microbe is anaerobic the particulate material has an operating interfacial surface area of from about 2,000 to about 240,000 square meters per cubic meter of reactor volume. When the microbe is aerobic the particulate material has an operating interfacial surface area of from about 1,000 to about 30,000 square meters per cubic meter of reactor volume. The method further includes establishing a flow of the reactant through the particulate material effective to contact the reactant with the microbes for a time sufficient to chemically modify the reactant. Use of the methods in wastewater treatment, aquaculture fish production, and ethanol production are disclosed.

23 Claims, 17 Drawing Sheets

1

PROCESS FOR CHEMICAL MODIFICATION OF REACTANTS BY MICROBES

FIELD OF THE INVENTION

The present invention relates to a method for chemical modification of reactants using microbes.

BACKGROUND OF THE INVENTION

Bioreactors are growing in use for waste treatment, chemical synthesis, and other applications. Improvements in bioreactor design are needed to reduce costs and increase efficiencies.

Biological wastewater treatment systems began to use techniques to concentrate microbial biomass before the turn of the century. Sedimentation combined with pumped sludge return was the basis of the activated sludge process. This process is the most common biological wastewater treatment process in use today, and it differs little from the basic concept used more than 80 years ago. Recycle of suspended microbial solids in the sludge return enabled accumulation of 1 to 3 grams of microbial organic matter per liter of reactor (1 to 3 g VS/l,) Early efforts to concentrate and retain microbial biomass took advantage of the natural capability of microorganisms to form slimes or biofilms on surfaces. Use of these attached microbial film processes paralleled the development of the activated sludge process and resulted in a process referred to as "the trickling filter". Biofilms enable water to flow rapidly, while the microbes are retained on the surface, i.e., short water retention times and long solids retention times. However, these older biofilm processes still have limited microbial concentrations (1 to 3 g VS/l, in most cases) and, as a consequence, require long exposure to achieve the desired bioconversion. Several days' retention of sewage in activated sludge and large volumes in trickling filters, for example, are not uncommon. In addition, complex sedimentation systems are required for both activated sludge and trickling filters to control the solids and to produce the desired treated water quality.

Among the processes for treatment of waste water utilizing microbes are processes which use suspended microbes, such as in activated sludges, or which fix the microbes to stones, plates, and plastics, such as in the trickling filter and the rotating disk filter, often referred to as "rotating biological contactor" or "RBC". However, these microbial processes suffer from a number of drawbacks. In particular, although these processes make use of carriers with high surface areas, once the microbial film reaches equilibrium, the effective surface area is significantly reduced. For example, a commercially available process, the Chiyoda "Biofiner Process", based on U.S. Pat. Nos. 4,256,573 and 4,454,038, both to Shimodaira et al., employs tubular particles having overall dimensions of 5 cm long by 5 cm diameter which provides an effective surface area of approximately 600 m$^2$/m$^3$ once the biofilm has formed. This process achieves between 5 and 10% of the optimum microbial concentration that can be achieved by aerobic systems, and less than 3% of that achievable in anaerobic applications. In addition, at the high flow rates that are necessary for the operation of processes employing large particles, management of suspended solids is complicated.

Smaller particles, such as sand, have been used in bioreactors but these frequently become clogged with suspended solids. In addition, attached biofilms quickly bridge between particles, thus reducing the effective surface area of the biofilm.

To reduce operational problems, upflow bioreactors using small moving inert particles with densities greater than water were developed. Early upflow bioreactors, such as those described in U.S. Pat. Nos. 3,846,289, 3,956,129, 4,009,098, 4,009,099, and 4,009,105, all to Jeris, required high flow rates, which resulted in fluidized bed formation. Improvements in these processes, using lower flow rates and expanded beds, have been described in U.S. Pat. No. 4,284,508 to Jewell. However, the upflow moving particle reactors suffer from several limitations. Influent suspended solids concentrations must be limited with these upflow processes. Uniform inflow distribution and bed management is also difficult with dense particles. In practice, these considerations limit reactor diameter to between 2 and 5 meters. To match required retention time to achieve design conversion efficiency and to achieve proper flow distribution with these limited diameters, the height of a typical wastewater treatment unit may need to be greater than 100 meters, an unacceptable shape for most applications.

Moreover, upflow systems employing denser-than-water particles are typically incompatible with the existing systems which employ rectangular, relatively shallow tanks, common in activated sludge plants. Consequently, use of presently-available small-particle upflow systems for sewage treatment requires new construction. However, the market for waste management exists primarily in retrofitting existing facilities.

In addition to sewage treatment, bioreactors have been used to effect or proposed as a means of effecting a number of other chemical conversions. In particular, they have been used in aquaculture fish production. However, conventional bioreactors are not suitable for commercial scale use because the high density of fish common in such operations and the low efficiencies of existing bioreactors require extremely large bioreactors, frequently with volumes 300 to 3000% of the volume of the fish growing tank.

For these and other reasons, the need remains for a process in which microbes can chemically modify reactants in an economically efficient and practical manner.

SUMMARY OF THE INVENTION

This need is met by the present invention which relates to a process for chemical modification by microbes of a reactant.

In one aspect of the present invention, the process for chemically modifying a reactant includes providing a particulate material comprising a carrier and microbes attached to the carrier. The particulate material is dispersed in a dispersing fluid and has a specific gravity less than that of the dispersing fluid. When the microbe is anaerobic the particulate material has an operating interfacial surface area of from about 2,000 to about 240,000 square meters per cubic meter of reactor volume. When the microbe is aerobic the particulate material has an operating interfacial surface area of from about 1,000 to about 30,000 square meters per cubic meter of reactor volume. The method further includes establishing a flow of the reactant through the particulate material effective to contact the reactant with the microbes for a time sufficient to chemically modify the reactant.

In another aspect, the process for chemically modifying a reactant includes providing a particulate material in a dispersing fluid. The particulate material comprises a carrier and microbes attached to the carrier and has a specific gravity different than the specific gravity of the dispersing fluid. The method further includes establishing a flow of the reactant through the particulate material in the dispersing fluid effective to contact the reactant with the microbes for a time sufficient to chemically modify the reactant. The flow has a vertical component effective to form an expanded bed of the particulate material in the dispersing fluid as well as a horizontal component.

In another aspect, the present invention relates to a process for the chemical modification of a reactant by microbes, other than for the chemical modification of wastewater components having biological oxygen demand. The method includes providing a particulate material comprising a carrier and microbes attached to the carrier. When the microbe is anaerobic the particulate material has an operating interfacial surface area of from about 2,000 to about 240,000 square meters per cubic meter of reactor volume. When the microbe is aerobic the particulate material has an operating interfacial surface area of from about 1,000 to about 30,000 square meters per cubic meter of reactor volume. The method further includes establishing a flow of the reactant through the particulate material effective to contact the reactant with the microbes for a time sufficient to chemically modify the reactant.

The chemical modification process of the present invention permits efficient and rapid modification of a variety of reactants. The method is particularly useful to treat sewage, to treat groundwater toxics, and to nitrify and denitrify the water used in aquaculture fish production. Using the methods of the present invention, bioreactors having much shorter hydraulic retention times relative to conventional processes are possible. These shorter retention times permit aquaculture production of fish using recycled waters which makes such production economically efficient, particularly in environments where water is scarce. In sewage treatment applications, using the methods of the present invention, hydraulic retention times as short as several minutes are possible. Furthermore, the exceptionally high interfacial surface areas used in the methods of the present invention permit the use of organisms in processes which have relatively low biochemical conversion rates. In addition, using methods of the present invention with horizontal as well as vertical flow, head loss through the bed, suspended solids management, and biofilm management can each be optimized in a single bioreactor.

BRIEF DESCRIPTION OF THE DRAWINGS

FIG. 10A shows influent and effluent VOC's during a one month period at 18–20 degrees C. FIG. 10B shows influent COD and VFA during the time of operation. FIG. 10C shows the percent of effluent VOC as ethene versus expanded bed HRT during runs at 20 degrees C.

FIG. 12A at 40° C., FIG. 12B at 35° C., FIG. 12C at 30° C., FIG. 12D at 25° C., FIG. 12E at 20° C., FIG. 12F at 15° C., FIG. 12G at 10° C., FIG. 12H at 50° C. The viscosity, v, of the water at these temperatures is indicated. Curves correspond to particles having different specific gravities. Curve number, specific gravity of particle: 1, 1.001; 2, 1.002; 3, 1.005; 4, 1.01; 5, 1.05; 6, 1.10; 7, 1.50; 8, 2.00; 9, 2.65. Experiments show that 1 mm STYROFOAM™ particles have rise velocities similar to the settling velocities of particles having gravities of 1.5 (curves 7).

DETAILED DESCRIPTION OF THE INVENTION

Figure 1:
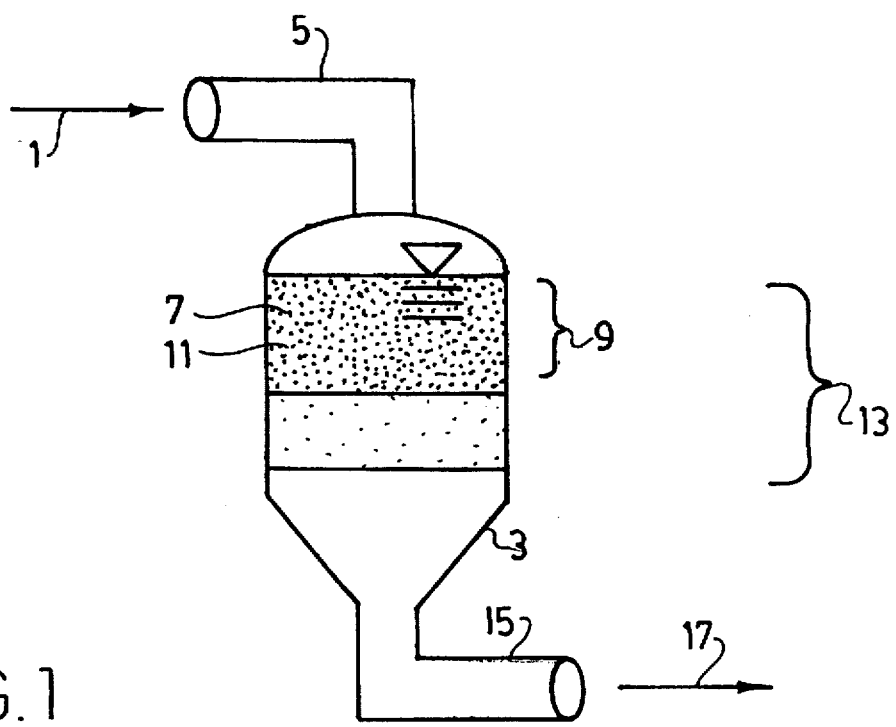
FIG. 1 illustrates one embodiment of the process of the present invention using a buoyant particulate material and a downflow of reactant.

The present invention relates to a process for chemical modification of a reactant by microbes.

In one aspect of the present invention, the process for chemically modifying a reactant includes providing a particulate material comprising a carrier and microbes attached to the carrier. When the microbe is anaerobic the particulate material has an operating interfacial surface area of from about 2,000 to about 240,000 square meters per cubic meter of reactor volume, preferably from about 4,000 to about 24,000 square meters per cubic meter of reactor volume. When the microbe is aerobic the particulate material has an operating interfacial surface area of from about 1,000 to about 30,000 square meters per cubic meter of reactor volume, preferably from about 2,000 to about 6,000 square meters per cubic meter of reactor volume. The method further includes establishing a flow of the reactant through the particulate material effective to contact the reactant with the microbes for a time sufficient to chemically modify the reactant.

In another aspect of the invention, the particulate material is dispersed in a dispersing fluid and has a specific gravity less than the specific gravity of the dispersing fluid.

The present invention also relates to a process where the chemical modification of the reactant is other than the chemical modification of wastewater having biological oxygen demand. Chemical modifications of reactants other than wastewater having biological oxygen demand includes chemical denitrification and nitrification of water, such as that used in aquaculture fish production, ground water detoxification, and the biosynthesis of organic molecules from organic reactants.

In another aspect, the process for chemically modifying a reactant includes providing a particulate material in a dispersing fluid. The particulate material comprises a carrier and microbes attached to the carrier and the particulate material has a specific gravity different than the specific gravity of the dispersing fluid. The method further includes establishing a flow of the reactant through the particulate material in the dispersing fluid effective to contact the reactant with the microbes for a time sufficient to chemically modify the reactant. The flow has a vertical component effective to form an expanded bed of the particulate material in the dispersing fluid as well as a horizontal component.

Although it will be generally advantageous for the particulate material to be dispersed in a fluid, this is not necessary. Where a dispersing fluid is used, the fluid can be a gas or a liquid. Suitable liquids which can be used as dispersing fluids include water, oils, and solvents, such as alcohols, lower alkanes, and chlorinated hydrocarbons. The main consideration in the selection of an appropriate dispersing fluid, where one is used, is that it be compatible with the microbes (i.e. that it be non-toxic and capable of sustaining microbial viability and activity). Other considerations include the specific gravity of the dispersing fluid, especially in relation to the specific gravity of the particulate material employed, as discussed below; compatibility with the reactant and fluid in which the reactant is carried ("carrier fluid"), such as miscibility and absence of reactivity therewith; and cost. Typically the preferred dispersing fluid is water. As used in the context of the dispersing fluid, water includes purer forms of water, such as distilled water and deionized water, as well as seawater and other solutions and suspensions of water and other materials, such as surfactants, salts, buffers, solvents, and the like. Where anaerobic bacteria are employed, it may be advantageous to use fluids having low oxygen solubility or to incorporate oxygen scavengers into the dispersing fluid.

The particulate material comprises a carrier and microbes attached to the carrier. Microbes suitable for the practice of the present invention include bacteria, viruses, yeast, fungi, protozoa, plant cells, and animal cells. Selection of a particular microbe for a particular application is based upon a number of factors which will be apparent to those skilled in the art, such as the nature of the reactant being converted, the necessary conversion efficiency, the availability of microbes capable of effecting the conversion, the conditions under which the reaction is to be conducted (temperature, presence or absence of oxygen, presence or absence of other materials contaminating the reactant or byproducts of the reaction which are toxic to the microbes), the carrier employed, and the ease of attaching the microbes to the carrier. By way of illustration, microbes suitable for the treatment of wastewater include aerobic bacteria, such as nitrifiers and methanotrophs, and anaerobic bacteria, such as acetogens and methanogens. Where the reactant is ammonia, such as ammonia produced as a waste product in aquaculture fish production, microbes capable of effecting nitrification include Nitrosomonas and Nitrobacter. Denitrification of nitrate reactants can be effected using a variety of denitrifiers, such as Pseudomonas. A number of microbes have been employed in the biosynthesis of organic molecules from organic reactants. For example, microbes are employed in the production of alcohols, such as ethanol, from sugars (such as glucose, fructose, sucrose, and xylose), starches, and cellulose. A number of microbes have been employed in these conversions, including yeast (such as *Saccharomyces cerevisiae*), *Clostridium thermocellum*, *Thermoanaerubacter ethanolicus*, and, preferably, *Zymononas mobilis*. The present invention also contemplates the use of microbes genetically engineered to effect conversions which, at present, are typically conducted in batch processes, as described, for example, in Martin, ed., *Bioconversion of Waste Materials to Industrial Products*, New York : Elsevier Applied Science, 1991, which is hereby incorporated by reference. Such conversions can be used, for example, to produce vitamin $B_{12}$ (Corrinoide), ubiquinone, and acetic acid. The methods of the present invention are particularly suitable to effect conversion of raw feedstocks to biologically active therapeutics, such as drugs. These biologically active therapeutics include human insulin, digitalis, vaccines, parathyroid hormones, and monoclonal antibodies.

When the microbe is anaerobic the particulate material has an operating interfacial surface area of from about 2,000 to about 240,000 square meters per cubic meter of reactor volume, preferably from about 4,000 to about 24,000 square meters per cubic meter of reactor volume. When the microbe is aerobic the particulate material has an operating interfacial surface area of from about 1,000 to about 30,000 square meters per cubic meter of reactor volume, preferably from about 2,000 to about 6,000 square meters per cubic meter of reactor volume. As used herein particulate material volume means the volume which the particles occupy, including the volume of the particles themselves and the interparticle spaces, during operation of the process. In cases where the bed is expanded (i.e. where the interparticle spaces increase relative to a static bed as a result of flow of the reactant through the particulate material), the particulate material volume is the volume occupied by the particles and the increased interparticle volumes.

The particulate material used in the practice of the present invention can be provided in a number of ways. One way is to obtain the material from a reactor which has been in operation. Another way is to prepare the particulate material by attaching the microbes to the carrier. The means by which the microbes are attached to the carrier is not critical to the practice of the present invention. Typically, microbes form films on surfaces of almost any material with which they are in contact during replication without regard to the material's surface morphology (i.e. without regard to whether the surface is smooth, creased, or roughened). Consequently, the easiest way in which to attach microbes to the carrier is to expose the carrier to microbes under conditions effective for the microbes to attach to the carrier surface and effective for the microbes to replicate. This replication can be effected during the practice of and as part of the process of the present invention, in which case efficiencies, of course, will be reduced during the time in which microbial equilibrium is established, or replication can be effected separately and completed prior to use of the particulate material in the practice of the present invention.

Although in some instances, particularly in natural processes (such as nitrification of ammonia-rich waste, fermentation of sugars, and biodegradation of sewage), the reactant is naturally accompanied by a small amount of the microbe to be employed in the chemical modification, it is typically advantageous to seed the carrier with higher concentrations of microbe during start-up or at times when inhibitory conditions exist. These higher concentrations of appropriate microbes can be obtained from a variety of sources known to those skilled in the art. For example, anaerobic methane producing bacteria, useful in the anaerobic treatment of sewage, can be obtained from anaerobically digested sludge or from bovine rumen fluid. Nitrifying bacteria, suitable for the treatment of ammonia-rich aquaculture waste, can be obtained in concentrated form by removing biofilms from on-going aquaculture biofilters or from freshwater or marine sediments. Microbes used in the practice of the present invention to biosynthesize organic molecules from organic reactants, such as ethanol from glucose, can be obtained in concentrated form from conventional biosynthetic processes, such as from conventional fermentation broth. After seeding the carrier, conditions are maintained which are effective for microbial population growth. As the microbe population increases, the microbes naturally form films on the surface of the carrier which reach an equilibrium thickness in several weeks. The thickness of the microbial film at equilibrium depends primarily on the type of microbe. Where the microbe is aerobic, films suitable for the practice of the present invention have a thickness of from about 50 μ to about 500 μ. Where the microbe is anaerobic, films suitable for the practice of the present invention have a thickness of from about 5 μ to about 100 μ. Film thickness can be controlled by any of the methods which are used in conventional bioreactors, such as by the use of continuous or intermittent shearing forces, as described, for example, in Charcklis, et al., *Biofilms*, New York : John Wiley and Sons, Inc., p. 676 (1990), which is hereby incorporated by reference.

Preferably the carrier as well as the particulate material employed in the present invention is substantially spherical. As explained in detail below, a parameter in processes using microbes attached to carriers to effect chemical modifications to reactants is the operating interfacial surface area. The size of the carrier, therefore, is preferably selected such that the surface area of the particulate material (i.e. the area of the surface of the microbial film on the carrier) is from about 2,000 $m^2/m^3$ to about 240,000 $m^2/m^3$ in cases where the microbe is anaerobic, and from about 1,000 $m^2/m^3$ to about 30,000 $m^2/m^3$ in cases where the microbe is aerobic. Where the particulate material has the preferred substantially spherical shape, preferred average particle diameters (i.e. twice the sum of the carrier radius and the thickness of the microbial film) are from about 0.02 mm to about 2 mm, preferably from about 0.02 to about 1.2 mm, in cases where the microbe is anaerobic, and from about 0.2 mm to about 2 mm, preferably from about 0.3 to about 1 mm, in cases where the microbe is aerobic. Where the preferred anaerobic and aerobic film thicknesses are employed, carrier diameters ranging from 0.05 mm to about 1.2 mm and from 0.1 mm to 1.4 mm, respectively, are preferred.

A number of materials can be used as a carrier in practicing the process of the present invention. Illustrative examples of suitable lighter-than-water materials are solid plastics, gas-entrained plastics, such as STYROFOAM™, natural materials, such as cork, wood, closed-pore pumice, fused silica products, such as closed-cell CELITE™ and PERLITE™, and other materials that are non-soluble in the dispersing fluid and non-toxic to the microbe used. In addition, composite materials can be useful for multiple chemical manipulations, such as fixing activated carbon to plastic particles or ion exchange resins. Suitable denser-than-water materials include open-cell plastics, sand, open-cell CELITE™, fused diatomaceous earth, granular and powdered activated carbon, rock pumice, and mixtures of materials, such as composites of plastics and inorganic materials. A number of factors which influence carrier selection have already been discussed. Another parameter which should be considered in carrier selection is the effect of the carrier on particle management. A variety of factors affect the propensity of the particulate material to escape with the effluent. These factors include particle size, particle density, particle shape, and the settling or rise velocity of the particle. The rise or settling velocity characteristic of particles, in turn, is dependent upon viscosity of the dispersing fluid, temperature, and particle density. In terms of optimizing particle density for particle management purposes, particles which permit high reactant flow rates with minimum bed expansion and head loss are ideal. In these terms, where the process involves the use of particulate matter having densities greater than that of the dispersing fluid, it is desirable to use carriers having densities of from about 100.5% to about 260% of the density of the dispersing fluid, and, where the dispersing fluid is water, from about 1.005 g/mL to about 2.6 g/mL. In the case where the process involves the use of particulate material having densities less than that of the dispersing fluid, suitable carriers are those having densities of from about 2% to about 95% of the density of the dispersing fluid. Where the dispersing fluid is water, carriers having densities from about 0.02 g/mL to about 0.95 g/mL are suitable, and, in particular, carriers made of a foamed plastic having densities from about 0.02 g/mL to about 0.95 g/mL. Suitable foamed plastics include polyurethane and, particularly, expanded polystyrene, which is marketed under the tradename STYROFOAM™. Many suitable carriers are commercially available.

Although most chemical modifications of reactants using microbes involve reactants in solution, or suspension, or otherwise dispersed in some inert medium, the methods of the present invention are equally applicable to liquid reactants and gaseous reactants. Examples of gaseous reactants which have been chemically modified by conventional microbial methods and which gaseous reactants are suitable for use in the methods of the present invention include odorous gaseous effluents from composting and metal cleaning operations.

Preferably, the reactant is dispersed in a carrier fluid. The carrier fluid is preferably miscible with and compatible (e.g. non-reactive) with the dispersing fluid, where a dispersing fluid is used, and ideally, is the same as the dispersing fluid. Of course the carrier fluid must not interfere with the reactivity of or be toxic to the microbes employed in the process. Suitable carrier fluids include gases, such as air, nitrogen, and methane, as well as liquids, such as water and solvents. The preferred carrier fluid is water. Water, as used in the context of a carrier fluid, includes aqueous solutions and suspensions of other materials, such as salts, buffers, surfactants, solvents, and the like. The carrier fluid can also contain other materials which are necessary or desirable in effecting the chemical modification. For example, where the chemical modification is nitrification, the carrier fluid can advantageously contains an amount of dissolved oxygen effective to effect nitrification. Alternatively, where the chemical modification is denitrification of nitrite, incorporation of biodegradable organic matter, preferably in the amount necessary to convert nitrate to nitrogen gas, in the carrier fluid is desirable. In chemical modifications utilizing anaerobic microbes, the carrier fluid can contain oxygen scavengers.

The reactant can be present in any concentration in the carrier fluid, and, with few exceptions, preferably, is as concentrated as practicable. One exception is in the case where the byproduct of reaction is toxic to the microbe or interferes with the reactivity of the microbe with the reactant. Another exception is in the case where a product of reaction is a gas, in which case concentrated reactant may result in excessive agitation, which could, for example, damage the microbial film. In these cases, the reactant concentration can be optimized by conventional empirical means.

The flow of the reactant through the particulate material can be established by any of the conventional methods for moving gases, liquids, and fluids, such as by the use of pumps or by gravity. Free overflow weirs or submerged weirs can be used to distribute inflow or for recycle purposes. Submerged orifices can also be used to distribute flow across the bed. Each distribution point creates a "zone of influence" and a number of distribution points is desirable to expand the bed and effect uniform distribution of the flow around each particle in the particulate material. Intermittent higher flows may be useful to "bump" the bed to prevent interparticle solidification, to remove suspended solids, or to control headloss through the bed. Effluent recycle can be used for bed management purposes, preferably with return flows limited to less than five times the influent flow rate. Higher recycle rates may be useful when adding or removing materials with differential solubilities, such as $CO_2$, $N_2$, $CH_4$, or volatile organics (e.g. trichloroethylene). Optimization of flow rates depends primarily on the characteristic reaction rate of the microbe with the reactant, the concentration of the reactant, the operating interfacial surface area of the particulate material, and the density of the particulate material relative to the fluid in which it is dispersed. Where the carrier is STYROFOAM™, suitable flow rates are from 0.004 to 4.3 $m^3/m^2$-min, preferably from 0.004 to 1.7 $m^3/m^2$-min for anaerobic microbes and from 0.16 to 4.3, preferably from 0.16 to 1.7 $m^3/m^2$-min for aerobic microbes. The flow can have both a vertical and a horizontal component. The vertical component can be either upward or downward. In cases where the particulate material has a specific gravity greater than that of the dispersing fluid, a upward vertical flow effective to form an expanded bed is preferred. Alternatively, a downward vertical flow effective to form an expanded bed is advantageous where the particulate material has a specific gravity less than the specific gravity of the dispersing fluid. Bed expansion is desirable to permit flow of the reactant without turbulence or compaction and physical abrasion of the particulate material, both of which are believed to cause the microbes to slough off the carrier and, thus, reduce the effectiveness of the process. However, bed expansion, by increasing the particulate material volume(by increasing the interparticle spacing) also reduces the particulate material's operating interfacial surface area, thus also decreasing the efficiency of the modification process. Optimization of flow rates is achieved by balancing these competing effects.

Where the flow of the reactant is in the same direction as the natural migration of the particulate material in the fluid (i.e. upward in the case of buoyant particles and downward in the case of settling particles), compaction of the particulate material in a static bed, and clogging of that bed, is often encountered. Such clogging frequently results in reduced flow and increased headloss. The adverse effects of these undesirable phenomena can be minimized by conventional techniques, such as by intermittently reversing the flow, so as dislodge the clogging debris and disrupting the compaction.

In addition to the vertical component to flow, the flow can also have a horizontal component. By horizontal component, it is meant that the reactant flow, averaged over all reactant flow paths through the particulate material, exhibits a horizontal displacement. Generally, the benefits of horizontal flow increase with increasing horizontal component, and are appreciable when the ratio of the horizontal component to the vertical component (i.e. the distance traveled horizontally to the distance traveled vertically by the reactant) exceeds 2:1. Preferably, the horizontal to vertical flow component ratio is between 3:1 and 10:1.

The method of the present invention whether employing both horizontal and vertical flow or vertical flow alone, can, in addition, include recirculating a portion of the partially modified reactant from a downstream flow region to an upstream flow region. Such recycling of reactant can be used, for example, to control headloss, bed expansion, suspended solids accumulation, and biofilm accumulation.

In addition to providing a method by which reactants can be chemically modified by microbes, the method of the present invention also permits the efficient separation of suspended particles in the reactant medium. This feature is particularly advantageous in the treatment of wastewater which frequently contains a large amount of suspended solids which must be removed. Since filtration of suspended solids is strictly a physical phenomenon, and is not dependent on the presence or absence of microbes attached to the carrier, the method of the present invention could be modified by using particulate material, devoid of microbes, of the sizes described herein, to maximize suspended solids filtration, such as for clarification of drinking water. The particulate material can be lighter or heavier than the fluid in which it is suspended, and can be used in an upflow or downflow process, as described above.

Now with reference to the drawings, the process of the invention will be further explained to make it more understandable.

In FIG. 1, reactant 1 is introduced into apparatus 3 for chemical modification of reactants by microbes through inflow tube 5 at the top of apparatus 3. Within apparatus 3, particulate material 7 is floating in the form of static bed 9 in dispersing fluid 11. The particulate material 7 has a specific gravity less than the specific gravity of dispersing fluid 11. Reactant 1 is supplied by adjusting the flow rate in such a way that the volume of particulate material 7 expands to form expanded bed 13. Reactant 1, flowing through expanded bed 13, contacts and is chemically modified by the microbes which form the surface of particulate material 7 and is discharged through outflow tube 15 as effluent 17.

Figure 2:
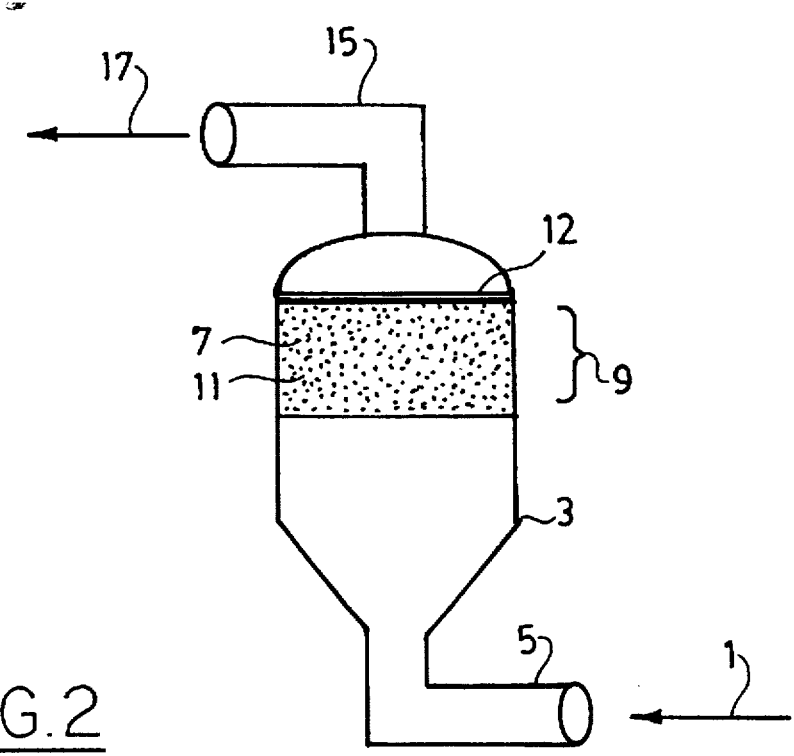
FIG. 2 illustrates another embodiment of the process of the present invention using a buoyant particulate material and a upward flow of reactant.

In FIG. 2, reactant 1 is introduced into bottom of the apparatus 3 for chemical modification of reactants by microbes through inflow tube 5. Within apparatus 3, particulate material 7 is floating in the form of static bed 9 in dispersing fluid 11. The particulate material 7 has a specific gravity less than the specific gravity of dispersing fluid 11 and is retained by bed retainer 12. Reactant 1, flowing upward through static bed 9, contacts and is chemically modified by the microbes which form the surface of particulate material 7 and is discharged through outflow tube 15 as effluent 17.

Figure 3:
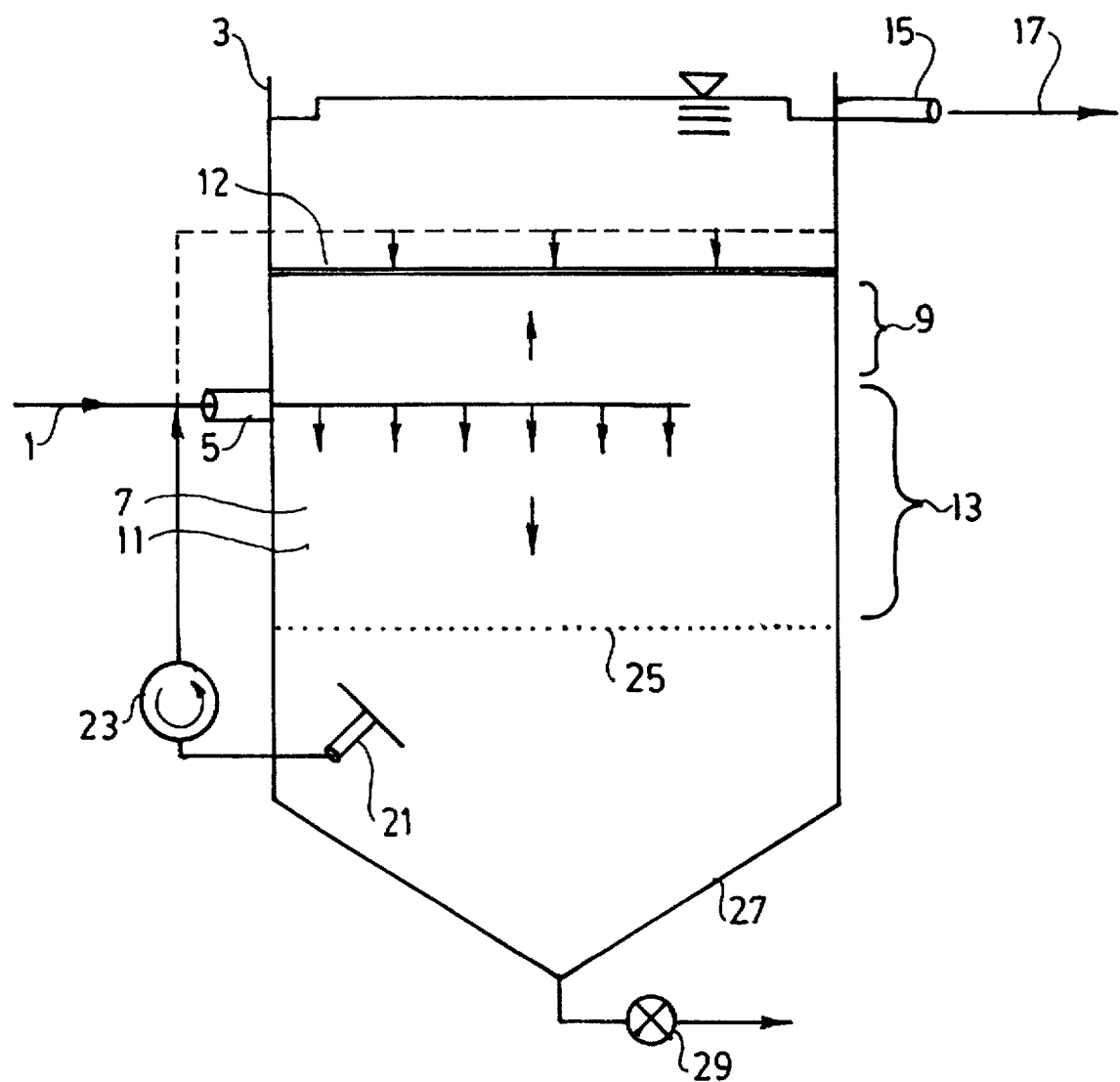
FIG. 3 illustrates another embodiment of the present invention using a buoyant particulate material and an upflow of reactant with a recycled counter-current downflow.

In FIG. 3, reactant 1 is introduced into apparatus 3 for chemical modification of reactants by microbes through inflow tube 5 at a position between the top and bottom of apparatus 3. Within apparatus 3, particulate material 7 is floating in the form of static bed in dispersing fluid 11. The particulate material 7 has a specific gravity less than the specific gravity of dispersing fluid 11 and is retained at the top of apparatus 3 by bed retainer 12. A portion of reactant 1, flowing upward through the portion of particulate material 7 above inflow tube 5 maintains the portion of particulate material 7 above inflow tube 5 in static bed 9. Reactant 1, flowing through static bed 9 contacts and is chemically modified by the microbes which form the surface of particulate material 7 in static bed 9 and is discharged through outflow tube 15 as effluent 17. A portion of reactant 1 is withdrawn through recycle tube 21 through pump 23 and returned via inflow tube 5 at a position between the top and bottom of apparatus 3. The counter-current flow rate established by pump 23 is adjusted in such a way that the volume of particulate material 7 below inflow tube 5 expands to form expanded bed 13. Reactant 1, flowing through expanded bed 13, contacts and is chemically modified by the microbes which form the surface of particulate material 7 in static bed 13. Recycle tube 21 is located below the bottom 25 of expanded bed 13. The flow of reactant 1 into apparatus 3 is adjusted in a way so that its flow rate is less than the counter-current flow rate. In applications where suspended solids accompany reactant 1, from time to time, a portion of the flow through inflow tube 5 is diverted to the top of bed retainer 12 to produce a short-duration downflow to dislodge suspended solids collected in static bed 9. In the process, suspended solids, migrate down through expanded bed 13, and are settle in the lower portion 27 of apparatus 3. From time to time, valve 29 is opened, whereby a portion of dispersing fluid 11 and reactant 1 is removed, flushing with therewith the suspended solids collected in the lower portion 27 of apparatus 3.

Figure 4:
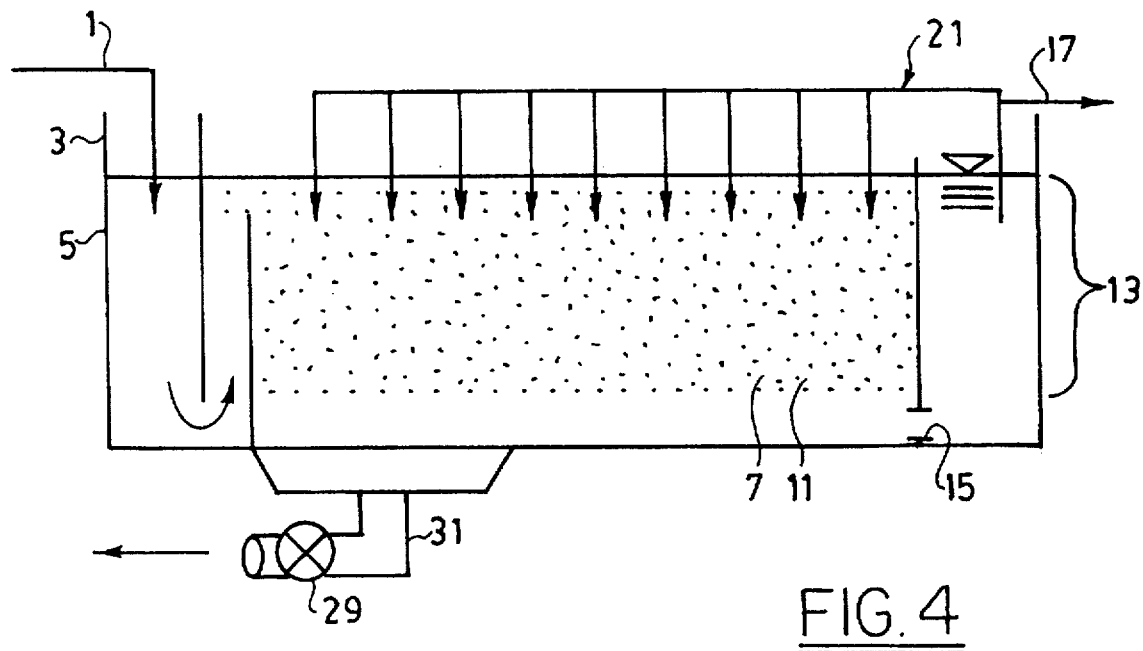
FIG. 4 illustrates an embodiment in which the reactant flow has a horizontal component.

In FIG. 4, reactant 1 is introduced into apparatus 3 for chemical modification of reactants by microbes through inflow tube 5 at the top of one end of apparatus 3. Within apparatus 3, particulate material 7 is floating in dispersing fluid 11. The particulate material 7 has a specific gravity less than the specific gravity of dispersing fluid 11. Discharge tube 15 is located at the bottom and at the opposite end of apparatus 3. The location of inflow tube and discharge tube necessitates that the reactant flow vertically downward and horizontally. Reactant 1 is supplied by adjusting the flow rate in such a way that the vertical downward component of the flow vertically expands the volume of particulate material 7 to form expanded bed 13. Reactant 1, flowing horizontally and vertically through expanded bed 13, contacts and is chemically modified by the microbes which form the surface of particulate material 7 and is discharged through outflow tube 15 as effluent 17. In applications where reactant 1 contains suspended solids, settled solids collect at the bottom of apparatus 3 and are swept out through solids removal tube 31 by opening valve 29 from time to time. To improve solids management, a portion of effluent 17 can be recycled through recycle tube 21. The apparatus is particularly useful to control suspended solids and headloss.

Figure 5:
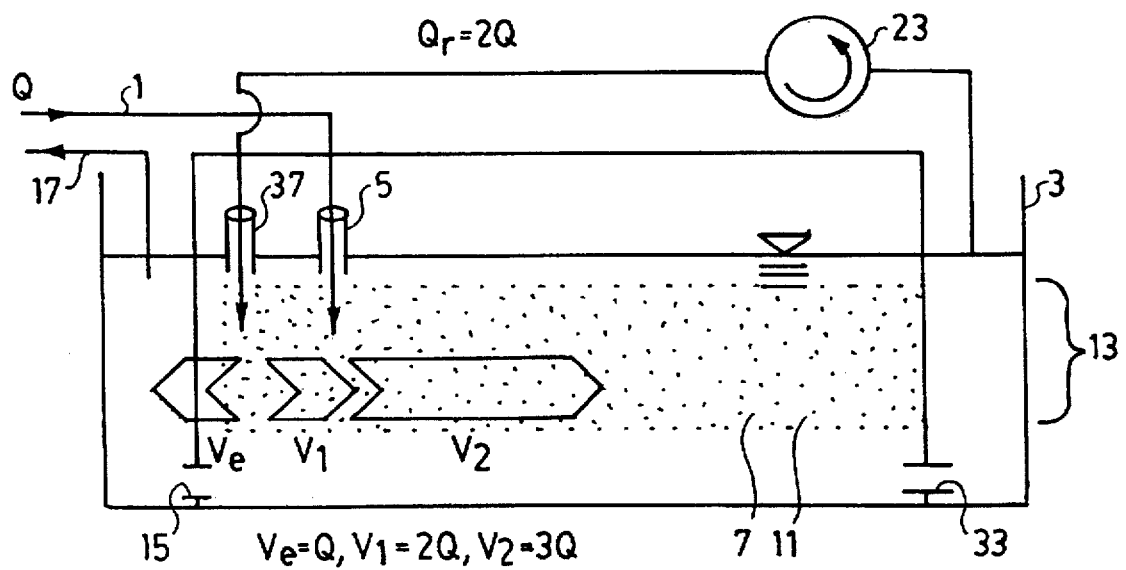
FIG. 5 illustrates an embodiment of the present invention with a reactant flow having a horizontal component and counter-current recycling.

In FIG. 5, reactant 1 is introduced into apparatus 3 for chemical modification of reactants by microbes through inflow tube 5 at a position near the top and near one end of apparatus 3. Within apparatus 3, particulate material 7 is floating in the form of static bed in dispersing fluid 11. The particulate material 7 has a specific gravity less than the specific gravity of dispersing fluid 11. Recycle tube 33 is located at the bottom and at the end of apparatus 3 distal to inflow tube 5. Discharge tube 15 is located at the bottom and at the end of apparatus 3 proximate to inflow tube 5. The location of inflow tube 5 recycle tube 33 and discharge tube 15 necessitates that the reactant flow vertically downward and horizontally. Reactant 1 is supplied by adjusting the flow rate in such a way that the vertical downward component of the flow vertically expands the volume of particulate material 7 to form expanded bed 13. Reactant 1 entering recycle tube 33 is recycled through pump 23 to recycle inflow tube 37. Recycle inflow tube 37 is located between inflow tube 5 and discharge tube 15. A portion of reactant 1 flows under the influence of pump 23 horizontally and vertically toward recycle tube 33 through expanded bed 13 and contacts and is chemically modified by the microbes which form the surface of particulate material 7. The remaining portion of reactant 1 flowing horizontally and vertically toward discharge tube 15 through expanded bed 13 contacts and is chemically modified by the microbes which form the surface of particulate material 7 and is discharged through outflow tube 15 as effluent 17. The additional horizontal flow from the recycle inflow tube to the recycle tube effects migration of suspended solids in this direction (i.e. away from discharge tube 15). This results in a very efficient separation of suspended solids as well as providing a means for controlling headloss. In addition, the horizontal configuration permits operation of the system at low flow rates which reduces undesirable agitation of the expanded bed and sloughing of the microbial films.

Figure 6:
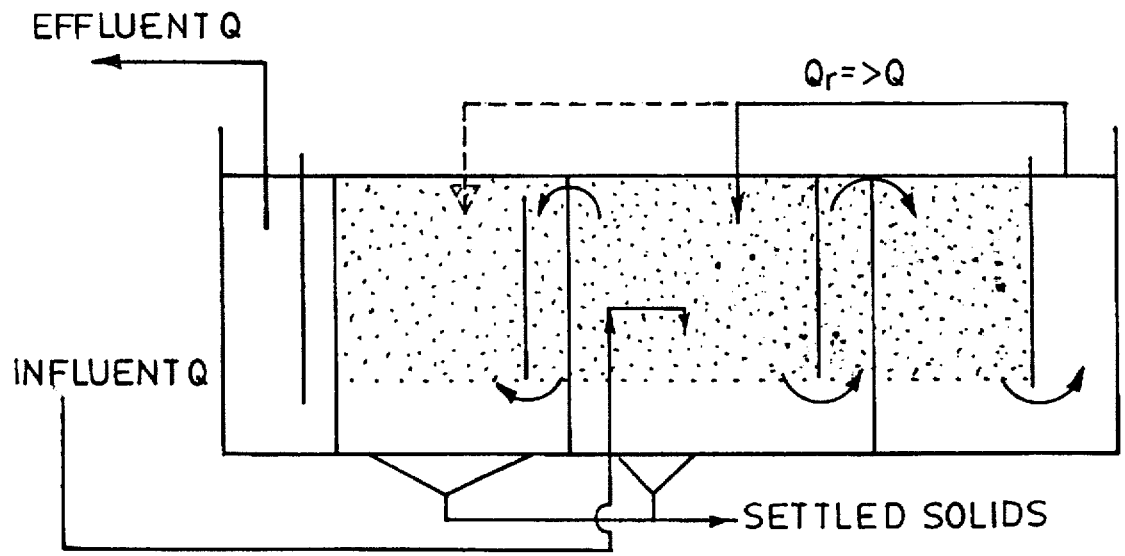
FIG. 6 illustrates a multi-cell horizontal floating bed with counter-current flow and upflow static bed clarification.

FIG. 6 shows a 3 compartment bioreactor apparatus particularly well-suited for applications where suspended solid removal is desired. The process features a two-chamber, series-arranged horizontal apparatus with counter-current flow and an upflow static bed which permits an additional clarifying step prior to effluent discharge. Intermittent recycle, indicated by the dashed line, to the clarifying static bed may be useful to control headloss and remove separated suspended solids.

The present invention is further illustrated by the following examples.

EXAMPLES

Example 1

Nitrification in aquaculture production recycle systems

Figure 7:
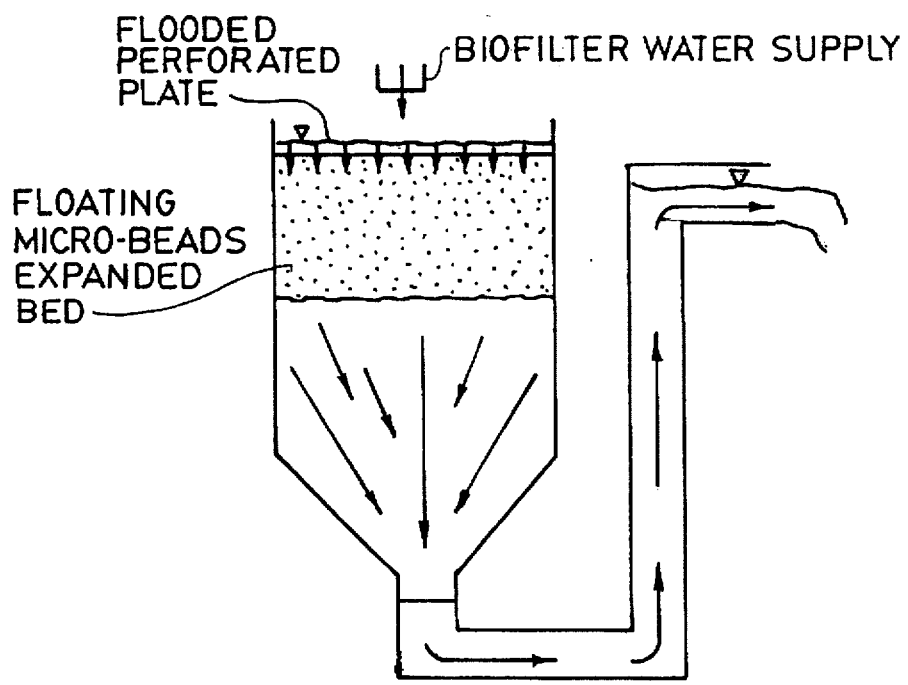
FIG. 7 is a drawing of the micro-bead nitrification filter used in Example 1.

A bench-scale study examined specific nitrification rates to apply to recycle fish production systems as described. The filter is shown in FIG. 7.

The floating carrier characteristics were as follows:

material: polystyrene, or STYROFOAM™ spheres;

diameter of carrier particle: 0.95 mm with standard deviation of 0.016 mm without biofilm;

biofilm thickness: less than 100 microns;

specific weight: 1 lb per cubic foot of dry and clean carrier;

porosity: 40%; and price: $2 per cubic foot

Influent was a synthetic aquaculture wastewater with ammonia-nitrogen concentrations varying from 1 mg/l to 10 mg/l. Average kinetics showed removal rates of 0.17 g $NH_4$—N oxidized to nitrates per square meter of surface area per day. This rate of nitrification supports the use of high velocities and hydraulic retention times as short as one minute.

Example 2

Nitrification of complete recycle aquaculture systems for Tilapia production.

Full-scale floating expanded bed modules were studied for tilapia production using a system similar to that shown in FIG. 7 and the same media used in Example 1, i.e., a 0.95 mm spherical STYROFOAM™ carrier. Floating beds with this media, were used with the flow rates presented in Table A for a period of six months or longer.

TABLE A

| Test Unit ID | Flowrate (gal/min) | Downflow Vel. (cm/sec) | Approx. Bed Expansion (% of static bed) |
|---|---|---|---|
| Unit 1 | 200 | 0.7 | 12 |
| Unit 2 | 300 | 1.03 | 22 |
| Unit 3 | 700 | 2.3 | 36 |

The above operating conditions provided an interfacial surface area of between 2,600 and 3,000 square meters surface area per cubic meter of reactor. The fish density and fish feeding rates that determined the recycle flow rate also fixed the total quantity of ammonia that was generated per day from the waste. For the 700 gallon per minute flow system, with a need to control ammonia at 0.5 mg/l, the total mass of the nitrogen that must be nitrified was 1900 grams per day. In order to make the system as economical as possible, all units were sized to have a hydraulic retention time of about 50 seconds. The one mm diameter STYROFOAM™ particle had an upflow velocity of 8 cm/sec. All of the downflow velocities employed (as listed in Table A) were compatible with the required downflow velocities at the remarkably short hydraulic retention time of less than a minute.

An examination of the interfacial biofilm loading rate showed that it is within the range of kinetics reported for nitrifying bacteria that-must operate very efficiently under low liquid concentrations. The volume of the bioreactor necessary to hold the 700 gal/min flow (2.65 cubic meters per minute or 3,820 cubic meters per day) for 50 seconds was 2.2 cubic meters. If it were necessary to purify the entire fish tank every hour (as was the case in these recycle systems), this biofilter volume is just a little greater than one percent of the volume of the fish production tank. This was a significant downsizing of a purification system compared to many conventional alternatives that are as big as the fish production vessel. The bed, maintained at a minimum expansion, had around 3,000 square meters per cubic meter of particulate material volume. Thus, the nitrification rate was around 0.28 g $NH_4$-N per square meter of biofilm surface area.

Long term operational trials have confirmed that the nitrification rate varied between 0.1 and 0.3 g $NH_4$-N per square meter of biofilm surface at 28=BOC for all conditions tested. Total resulting soluble nitrogen in the fish tanks were maintained at less than 1.0 mg/l for all test conditions. In addition, most of the biodegradable organic matter was degraded in the bioreactor.

Example 3
Combined nitrification and denitrification in a floating bed reactor for aquaculture systems Complete recycle systems must remove nitrogen or deal with the consequences of nitrate concentration accumulations. For this reason, even efficient nitrification units, such as that described in Example 2, must replace 5 to 10% of the water volume per day. Microbes for BOD reduction, nitrification, and denitrification were found to function in the same reactor, provided that the oxidation-reduction potential was controlled at the correct location in the reactor and the biofilm. Liquid was passed through the biofilter fast enough to support BOD removal and nitrification in the first section, was then denitrified with the small amount of remaining BOD. The effluent had very little remaining nitrogen, except in the $N_2$ gaseous form.

Figure 8:
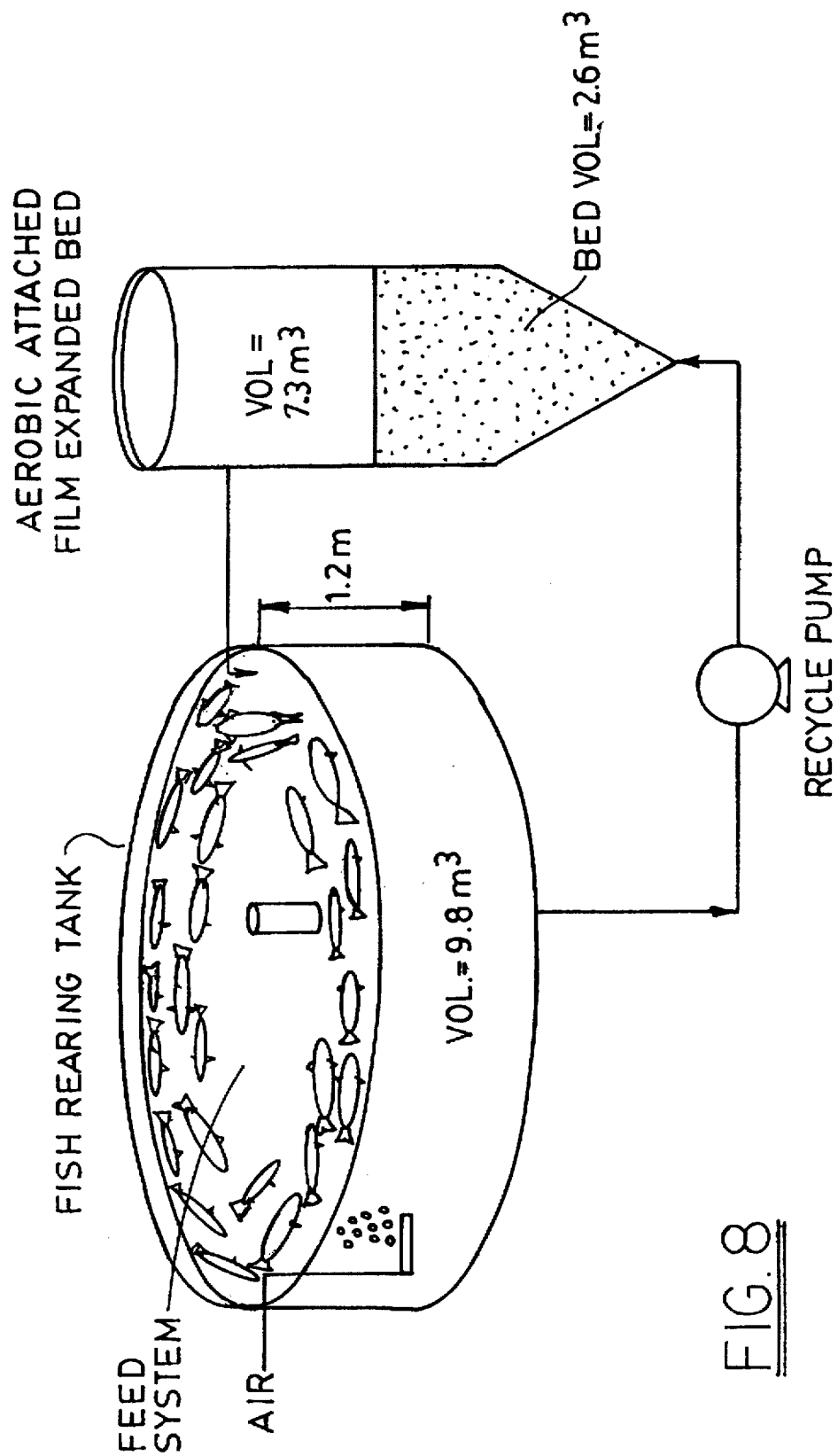
FIG. 8 is a schematic of the complete recycle aquaculture experimental test system used in Example 2.
Figure 9:
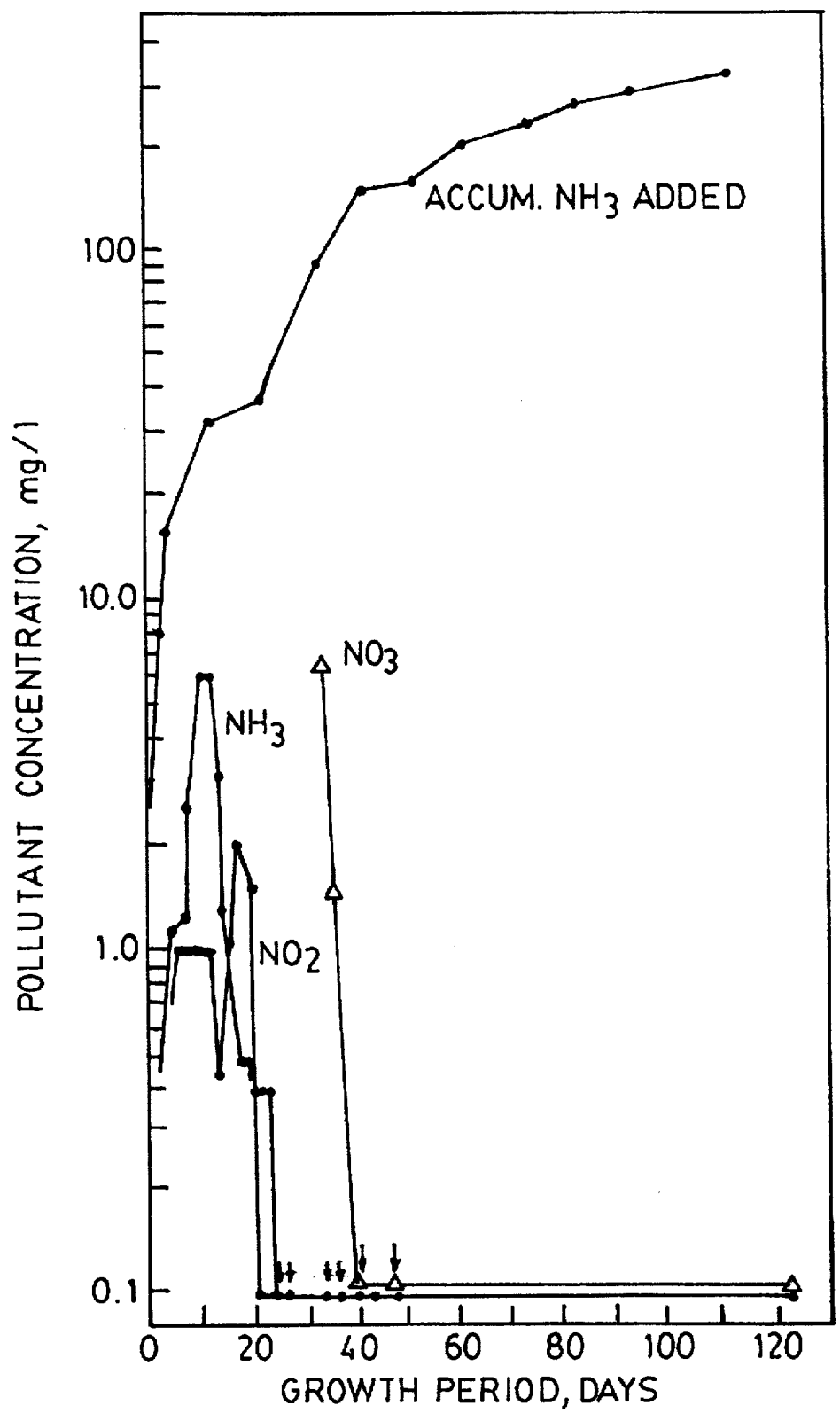
FIG. 9 is a graph showing the accumulative nitrogen added in the fish food to changes in soluble nitrogen in complete recycle Atlantic salmon production.

The full scale module was constructed and operated first with Atlantic salmon and then with trout. The module was operated in both an upflow mode with a diatomaceous earth particle having a diameter of 0.5 mm or less, and in a downflow mode with a floating bed composed of 1 mm STYROFOAM™ beads. The module is depicted in FIG. 8. Soluble nitrogen species resulting from the production of Atlantic salmon using the module of FIG. 8 are shown in FIG. 9. Throughout most of the four month growth phase, all species of nitrogen (nitrites, nitrates, and ammonia) were controlled below 0.1 mg/l. BOD and suspended solid values were below 10 mg/l throughout the growth phase.

Although this unit was not stressed to its limits, it demonstrates the possibility of achieving both aerobic and anaerobic nitrogen control simultaneously in a continuous flowing reactor. Further optimization of this technology can advantageously employ a separate denitrifying reactor because of the longer retention time required to deplete the dissolved oxygen to support the anoxic denitrification reaction.

Example 4
Sewage Treatment

Domestic sewage treatment is not thought to be possible because of the slow growth rate of anaerobic methanogenic bacteria. The low biodegradable organics in most household sewage and cold winter temperatures (as low as 7 to 8 degrees centigrade in the Northeastern U.S.) make it almost impossible to achieve good conversion. Estimation of the worst case conditions shows that the microbial solids must be retained longer than 300 days and biofilms must be loaded at a low rate to achieve efficient BOD conversion. For this reason, most experts dismiss anaerobic sewage treatment, or only consider it as a small part of a preliminary treatment system.

Given the requirement that the biofilm solids must be retained for nearly a year, an interfacial surface area loading rate was estimated based on the known biofilm mass on a surface. This was used to estimate required reactor volume for acceptable particle sizes. Using a biofilm having 5 g VS anaerobic biofilms per square meter of surface area and anaerobic yields as low as 0.1 g VS per g BOD removed, the required total interfacial surface was estimated. For a human population 10,000 people, the quantity of domestic sewage generated is typically 3,800 cubic meters per day containing 250 mg/l of BOD. The total required biofilm surface area was determined to be 5.6 million square meters. Using a particle that provides a biofilm surface area of 12,000 square meters per cubic meter in an expanded form, the total bioreactor volume was calculated to be 460 cubic meters. In such a bioreactor, the hydraulic retention period would be 2.9 hours.

Typical data from bench scale and pilot tests with both settling and floating particles that have 12,000 square meters per cubic meter for anaerobic treatment achieve BOD less than 30 mg/l and suspended solids less than 30 mg/l for temperatures varying from 12 to 30 degrees centigrade. Temperatures as low as 7 degrees centigrade may require a hydraulic retention time as long as six hours to achieve the above quality of effluents which is referred to as "secondary" quality effluent.

Example 5
Biochemical Ethanol Production

Two pure culture biofilms were used to estimate maximum ethanol production rates that could be generated from fermentation of sugars. Both used heavier than water, small diameter inert carriers. The yeast *Saccharomyces cerevisiae* was used with a bed composed of 197 to 297 micron diameter activated carbon particles. At 35 degrees C, and with a 0.75 hour hydraulic retention period, the maximum ethanol generation rate was 71 g/l-hr. The yeast biomass concentration was 106 g VSS/l.

The bacteria, *Zymomonas mobilis*, was chosen as a second test organism in an upflow expanded bed. The biofilm carrier was vermiculite with a diameter of 200–400μ. Ethanol production rates of 210 g/l-hr were achieved by a Zymomonas biofilm that achieved 60g VS/i.

Example 6
Expanded Bed Treatment of Common Groundwater Toxic Organics

The most common contaminant of groundwater are the volatile chlorinated organics, such as trichloroethylene ("TCE"). Until recently, these compounds were thought to be nonbiodegradable since they accumulate in the environment. It has been recently discovered that a very few anaerobic bacteria associated with methanogens can degrade these and other related compounds.

These toxic biodegrading reactions are relatively slow, and sometimes, the by-products are toxic to the bacteria. The low temperature of groundwaters also makes conventional application of methanogenic cultures questionable.

Figure 10A:
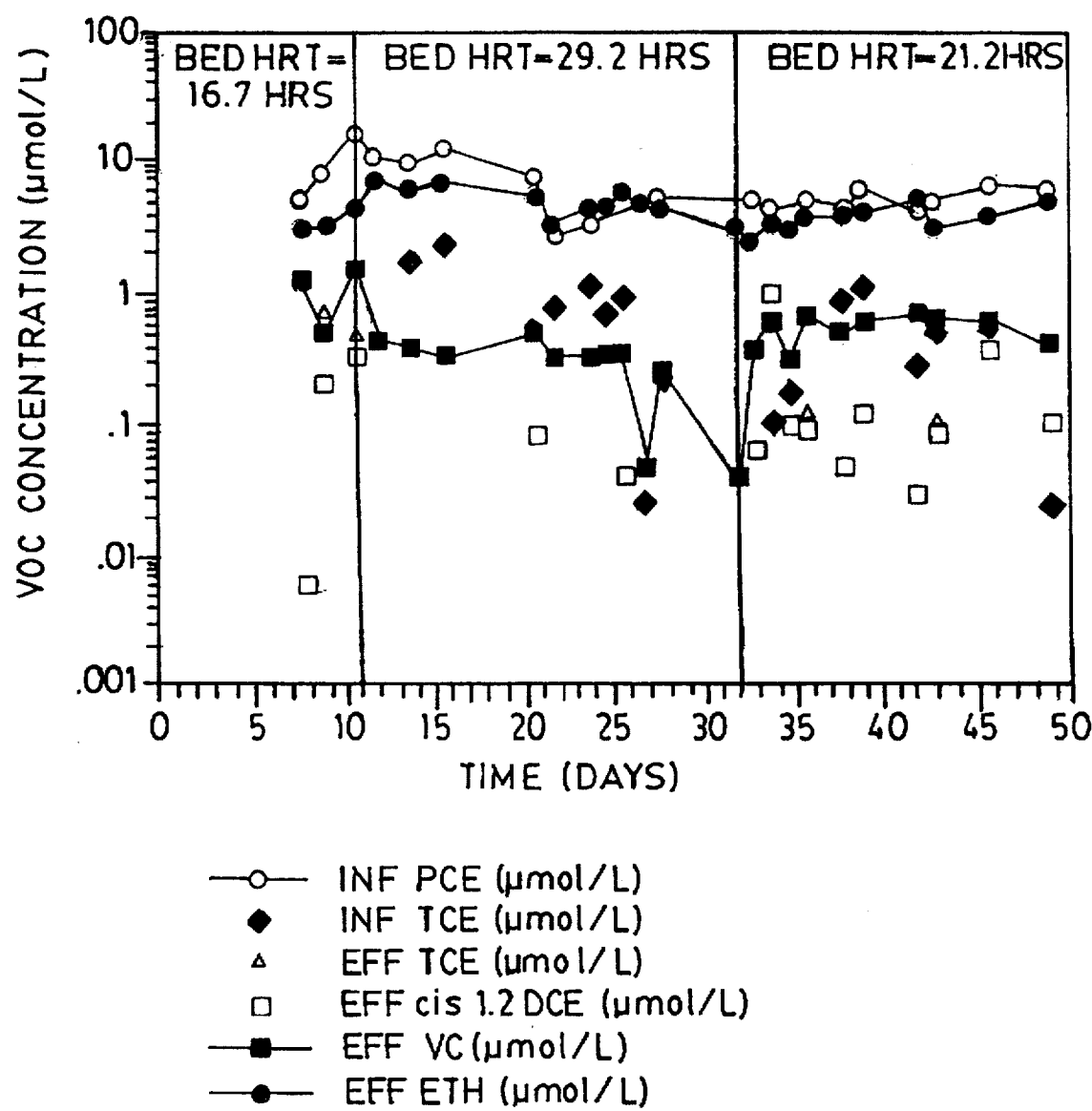
FIGS. 10A–10C are graphs showing the results of experiments described in Example 6 to remove toxic materials from water.
Figure 10B:
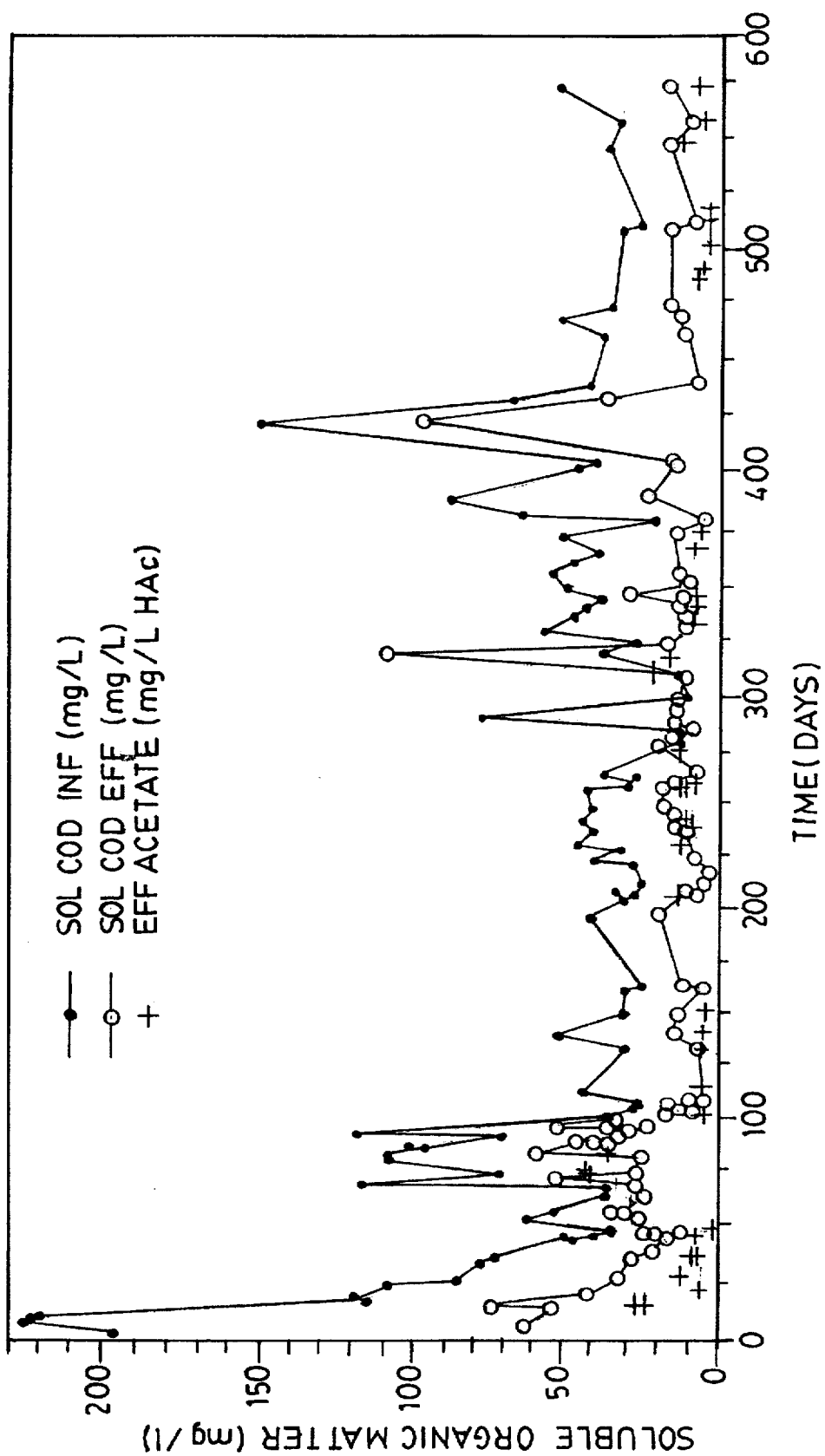
Figure 10C:
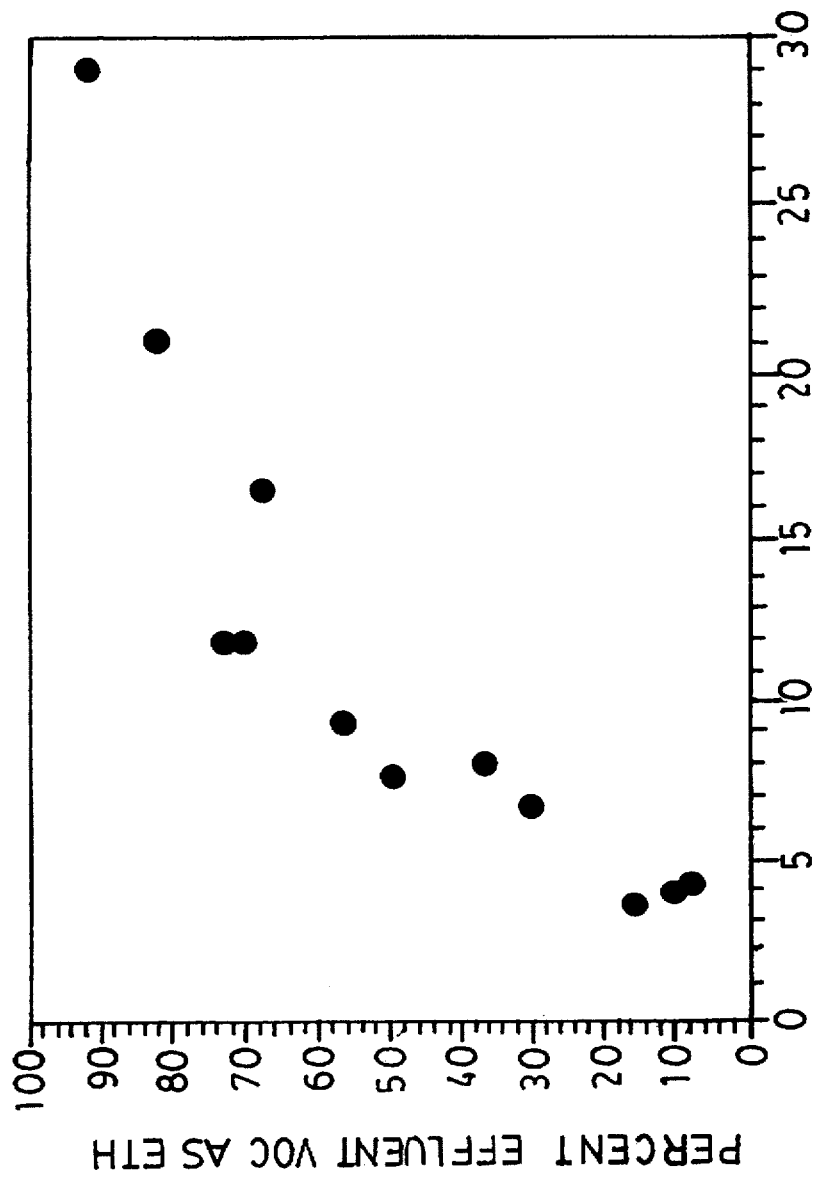

Typical data for a continuous flowing bench scale expanded bed bioreactor is given in FIGS. 10A–10C. A fused diatomaceous earth heavier-than-water carrier particle having a diameter varying from 0.3 to 0.8 mm was used. The process reduced these chlorinated compounds in a continuously flowing test to levels that met USEPA standards in reasonably short retention periods.

Based on the above information, a floating expanded bed was built to test this application. A one mm diameter STYROFOAM™ particle was used. Daily flows exceeded 2,000 gallons per day. Chlorinated ethenes were removed to less than 20 ppb at hydraulic retention periods of less than five hours. In addition, about ten other toxic organic compounds were removed. Significant metal concentrations were also removed by controlling them with biofilm formed by-products.

The following discussion of the features, design requirements and preferences, and uses of the methods of the present invention will serve to illustrate its advantages and flexibility and guide optimization of the process.

In the simplest terms, the best reactor will be the smallest reactor (assuming that added complexity does not change the unit volume costs significantly). The smallest reactor achievable will be the one with the largest concentration of microorganisms that can participate in the bioconversion reaction. In microbial parlance, this would be a bioreactor with the largest concentration of viable and actively metabolizing organisms. The history of waste treatment reflects continuous efforts to increase microbial concentrations thereby reducing the size and cost of treatment systems.

Development of bioreactors that used small movingparticle reactors increased the biomass concentration of attached microbial films. Expanded bed development was based on two premises. First, the largest surface area per unit of reactor that could be developed would result in an optimum reactor, as long as the liquid and solids could be effectively exposed to the liquid (or gases). Second, biofilms are fragile, and all designs must take this into account. This meant that individual biofilm-coated particles must be suspended by the flow in a relatively gentle manner. Grinding between particles and/or the reactor surfaces must be avoided to support attachment and maintenance of the fragile biofilms. Undue turbulence was also to be avoided (except where biofilm removal is desired). Thus early in the process development the term "expanded bed" was purposely chosen over the general process term of "fluidized beds." When the expanded bed is in operation, the particles appear "suspended" by the liquid or gas flow with relatively little interparticle motion. This is substantially different from the normal operations of a fluidized bed reactor which is highly turbulent, and in which the particles often approach a completely mixed state.

Over 20 years of R&D has demonstrated the superior capabilities of the attached film expanded bed ("AFEB"). Both aerobic and anaerobic applications have been developed, and biofilm characteristics have been documented. Maximum biomass concentrations in the expanded bed biofilms exceed 30 g VS/l, and 400 g VS/l, for aerobic and anaerobic applications, respectively.

There has been a great deal of research on biofilms; it is possible to design the reactors, predict film thickness, estimate biofilm shearing and loss and many other characteristics. However, it is still not possible to predict, with accuracy, biofilm densities, i.e., the dry matter or microbial mass per unit volume of film. This has been ignored for many applications, because many feel that it is not a controlling variable. Also, many studies with aerobic films report densities around 30 g VS/l, and, consequently, aerobic film density was assumed to be constant. If microbic biofilm densities do vary, the active biomass will also vary.

Anaerobic biofilms can achieve dry matter densities more than 10 times aerobic averages, and anaerobic films with densities greater than 400 g VS/l, have been reported. Recent work with aerobic films has shown that aerobic biofilms can also have densities greater than 30 g VS/l. The parameter controlling biofilm density is interfacial surface area loading rate (g of soluble food provided to the attached biofilm per unit area per unit time, e.g., g BOD per m² per day).

In this discussion, the limitations exerted by the movement of the soluble food through the film will be ignored (i.e., mass transfer barriers will not be considered significant). However, in optimizing the process of the present invention, it should be kept in mind that aerobic films can be very thick (i.e., greater than 200μ) and lead to mass transfer effects, whereas anaerobic films are almost always thin (less than 30μ), thus reducing the influence of carrier diffusion.

The thickness of the biofilm will dictate the practical lower limits for the size of the particles that can be used for any given application. Anaerobic films that reach an equilibrium thickness of 10 microns could function by attaching to particles as small as 10 or 20 μ in diameter, assuming that particles this small could be managed. Conversely, if an aerobic film is 200 μ thick, it is unlikely that very small particles could be obtained. This becomes an important consideration when the total available surface area created with various particle sizes is considered.

Since anaerobic films are dense and thin while aerobic films have the reverse properties, it is possible that the actual surface area concentrations (grams of microbial organic matter per unit surface area) may be quite comparable in all microbial systems.

Bioreactors should be designed on the basis of a theoretical understanding of the microbial kinetics of the bioconversion reactions of interest. In practice, this rarely has been the case, because basic knowledge was lacking. As a result bioreactors were often designed using simplistic parameters such as hydraulic retention times or volumetric loading rates. These parameters have been defined for many applications with an empirical basis under "real world" conditions and, thus, can be used with little risk where experience is sufficient.

Empirical design parameters, however, prevent the use of new and more efficient designs, since they offer little insight into the limiting parameters of the reaction(s). The following summarizes the advances in understanding of biofilm characteristics and illustrates how this increased understanding may be used to optimize the processes of the present invention in terms of biofilm reactor size and particulate material size and density.

Microbial kinetics define the capability to bioconvert materials over a wide range of conditions. Once an efficiency of conversion is determined, an understanding of the kinetics would permit sizing of the bioreactor and estimating by-product production, excess solids generation, etc.

A brief description of microbial growth kinetics and biofilm characteristics is given here to illustrate the state of understanding of the process of the present invention. Table 1 summarizes several concepts that will be used to describe bioreactor improvements. Microbial growth is described by enzyme kinetics. The speed or rate of a reaction is proportional to soluble feed concentration that surrounds a viable cell, until a maximum growth rate is achieved. Further increases in soluble feed concentration above the maximum have no effect on the growth rate; in fact, too great a concentration will become inhibitory and eventually toxic. The efficiency of the bioconversion reactor decreases with increased growth rate. Also, another critical bioreactor parameter that dictates the stability of the reactor system, the time that the microbes remain in the reactor (the solids retention time or "SRT"), also decreases with increased growth rate and decreased reactor efficiency (i.e., increased effluent soluble feed concentration).

TABLE 1

Summary of microbial kinetic models and definition of important parameters of bioreactor design I. Microbial Growth $$\frac{dx}{dt} = a\left(\frac{ds}{dt}\right) - bx$$

$\frac{dx}{dt}$ = microbial growth, mass/time = u $\frac{ds}{dt}$ = rate of waste utilization, mass/time x = mass microbes
a = growth rate coefficient
b = endogenous respiration rate coefficient II. Substitute Use $$\frac{ds}{dt} = \frac{U_{max}SX}{K_s + S}$$

$U_{max}$ = maximum growth rate
S = substrate cone
$K_s$ = waste concentration at which u = $U_{max}/2$ III. Microbial Growth Parameters
Y = yield = mg cells/mg substitute used $$\frac{dx}{dt} = y\frac{ds}{dt}$$

Solids retention time = SRT = $\frac{x}{dx/dt}$ $SRT_{min} = \frac{1}{U_{max}}$

In general, in pollution control systems, the greatest removal of a pollutant is the object of a process. Therefore, most pollution control systems are designed to achieve very efficient conversions. The key for cost-effective systems is to achieve the desired conversion in the lowest-cost system. The floating expanded bed can be utilized for this purpose when used in conjunction with the methods of the present invention.

High-efficiency reactors require low soluble feed concentrations and, therefore, low growth rates that result in long microbial SRTs. In addition, the greater the microbial mass per unit volume of reactor, the smaller the required size of the reactor necessary to achieve a given reaction rate.

Optimization of the process of the present invention involves consideration of several principles, some of which are noted above. Since the most concentrated form of microorganisms is in a biofilm, reactors employing biofilms are always the general reactor of choice (as opposed to using microbes maintained in suspension) for liquid and gas interaction.

Maximum biomass concentration is achieved, in principle, in a reactor filled with biofilm. This is an impractical upper limit since a reactor totally filled with microbes could not be arranged so that the reactant could move around the organisms and through the reactor. Thus some void space would be necessary, and some means of managing the organisms to separate them from the flow is required.

The above general considerations result in several important guidelines that are helpful in developing "the optimum bioreactor." T he optimum bioreactor will be that which accomplishes the highest unit volume rate of reaction at the highest conversion efficiency. It follows that this reactor must achieve the highest biomass concentrations, the longest SRT for the given application at the highest flow rate compatible with biofilm management. This latter parameter requires incorporation of cell separation as well as consideration of parameters necessary to enable biofilm reactors to function. A primary parameter is to note the fragile nature of natural biofilms. Conditions that minimize shearing of the biological slimes must be incorporated in bioreactor design. These include low velocities and the use of small, light particles that have high surface areas.

A review of biofilm literature shows a striking difference between aerobic and anaerobic films. Aerobic films are thicker and less dense than anaerobic films (mostly methane-forming films have been documented). Aerobic films have bulk densities nearly always around 30 g VS per liter of biofilm, whereas anaerobic methanogenic films have a highly varying density ranging from 100 to greater than 400 g VS/$l_f$. The higher value represents a higher dry matter density than most life forms at 40% dry matter.

A major controlling parameter with biofilms is the interfacial surface loading rate (e.g., g BOD per square meter of surface area per day). Low loadings result in thinner and more dense biofilms under both aerobic and anaerobic conditions. Thus in aerobic cases, when the interfacial surface area is high (such as in several methanotrophic applications), biofilm densities can be high, for example, greater than 150 g VS/$l_f$.

It is instructive to calculate biomass concentrations that occur in biofilms using the above values (see Table 2). The actual quantities of biomass in aerobic and anaerobic biofilms are quite similar, and vary less than 10-fold even though thicknesses and densities can vary over nearly a hundred-fold between extreme cases. For simplistic comparison purposes, biofilm mass concentration might even be considered equal at around 5 g VS/$M^2$ of surface area.

TABLE 2

Summary of general aerobic and anaerobic microbial biofilm characteristics

| | Aerobic Films | Anaerobic Films |
|---|---|---|
| A. Microbial Film Depths of Equilibrium depth in microns, $\mu$ | 100 to 400+ | 10 to 20 |
| B. Microbial Film Densities g VS per liter of biofilm | 30 (100+ in exceptional cases) | 100 to 400+ |
| C. Microbial Film Surface Accumulation at Equilibrium g VS per m$^2$ Surface area | 10 to 12 | 2 to 4 |

Note: The thicker aerobic biofilms may have mass transfer limitations, especially at low substrate concentrations. Thus, the active or viable biomass is probably less than this 10 to 12 g VS per m$^2$ total biofilm estimate.

The state of the art of biofilm characteristics is still not sufficient to predict the quantity of viable microorganisms per unit volume of a reactor operating with a specific particle size. Thus, a simplistic parameter, such as interfacial loading rate is used in describing the methods of the present invention and can be used until science catches up with engineering needs.

Validation of such an empirical approach would require comparison of the microbial kinetics to those on a surface area basis. This is discussed below.

An example of the relationship between fundamental microbial growth characteristics and how one could use interfacial loading rates is given in Table 3 for nitrification in a closed recycle aquaculture system. The basic microbial kinetic assumptions are from nitrification rate studies. Presently, most aquaculture systems require bioreactors that have hydraulic retention periods of several hours to days. It will be necessary to design the bioreactor to have a much shorter hydraulic retention period in order for closed system aquaculture to be economically attractive. A two-minute retention time is assumed in the example. When expanded to enable liquid to pass through the system, a particle diameter having around 1 mm diameter would be required, as noted in Table 3. SRT achieved by such a bioreactor is estimated to be 254 days. The remaining design consideration is to choose particles for the application that could be retained and easily managed at such high flow rates as would occur in a bioreactor with an HRT of two minutes.

Note that a study (Nijhof, et al., "Diffusional Transport Mechanisms and Biofilm Nitrification Characteristics Influencing Nitrate Levels in Nitrifying Trickling Filter Effluents,"*Water Research* 29:2287–2292 (1995), which is hereby incorporated by reference) of the fundamental characteristics of a nitrifying biofilm reported interfacial conversion rates between 0.1 and 0.2 $NH_3$—N per m$^2$ per day for conditions similar to those given in Table 3.

TABLE 3

Example of how particle size determination can be used to relate to fundamental microbial growth kinetics Example: Nitrification in closed system aquaculture.
Maximum operating concentration of $NH_3$—N of 0.5 mg/l
Problem: Estimated particle size required to obtain minimum size bioreactor for complete nitrification.

TABLE 3-continued

Example of how particle size determination can be used to relate to fundamental microbial growth kinetics Assumptions: Influent concentration of 0.5 mg/l $NH_3$—N
Designed reactor hydraulic retention time of 52 min.
Temperature of 20° C.
Nitrification rate of 14 mg $NH_3$—N converted per g VS per day
Biofilm surface area density of 10 g VS/m$^2$
Reactor expansion of 50%
Observed yield = 0.05 to .30 g VS per g $NH_3$—N oxidized $$NH_3\text{—N loading rate} = 0.5 \text{ mg } NH_3\text{—N/l} \times \frac{1}{1/2\min} \times 1440 \frac{\min}{d}$$

$$= \frac{360 \text{ mg } NH_3\text{—N}}{l_r - d} = \frac{360 \text{ g } NH_3\text{—N}}{m_r^3 - d}$$

$$\text{Required nitrifying microbial biomass} = \frac{\frac{360 \text{ g } NH_3\text{—N}}{m_r^3 - d}}{\frac{0.014 \text{ g } NH_3\text{—N}}{\text{g VS} - d}} = \frac{25700 \text{ g VS}}{m_r^3}$$

$$\text{Required biofilm surface area, SA} = \frac{\frac{25700 \text{ g VS}}{m_r^3}}{\frac{10 \text{ g VS}}{m^2}} = 2{,}570 \frac{m^2}{m_r^3}$$

Particle diameter required to provide surface area
Particle surface area/unit reaction volume = 3.61/D
where D is in meters
2750 m$^2$ = 3.61/D
D = 1.4 × 10$^{-3}$ m or 1.4 mm
Resulting interfacial surface area loading rate $$\text{SALAR} = \frac{\frac{360 \text{ g } NH_3\text{—NH}}{m_r^3 - d}}{\frac{2570 \text{ m}^2}{m_r^3}} = \frac{0.14 \text{ g } NH_3\text{—N}}{m^2_{biofilm} - d}$$

Resulting bioreactor SRT @ equilibrium $$\text{Microbial yield} = \frac{0.28 \text{ mg VS}}{mg_{cells} - d} \ (360 \text{ g/m}_r^3 - d) = \frac{101 \text{ g VS synthesized}}{m_r^3 - d}$$

$$\text{SRT} = \frac{\text{total mass}}{\text{net synthesis wasted per day}} = \frac{25700 \text{ g VS/m}_r^3}{101 \text{ g VS/m}_r^3 - d} = 254 \text{ days}$$

One major parameter controlling biofilm reactors is the interfacial surface area per unit volume of reactor. There is an intimate relationship between this parameter, particle size and density, and the settling or rise velocity of the material. The interrelationship of these parameters dictates the viability of a biofilm reactor. Most of the technology applied heretofore fail to recognize or apply these relationships, and this has resulted in highly nonoptimum designs or malfunctional processes.

Figure 11:
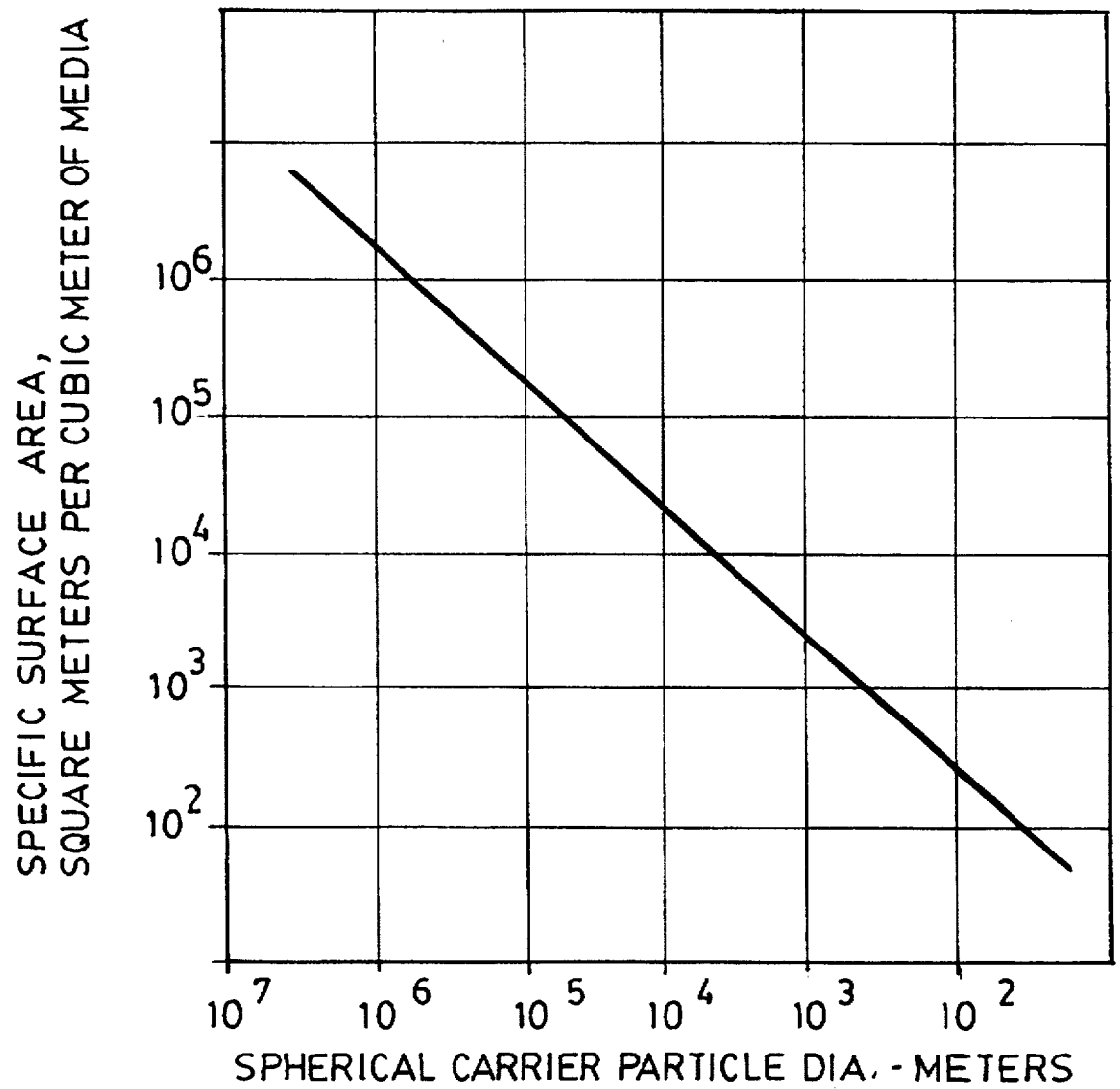
FIG. 11 is a graph of the relationship of particle diameter and specific surface area of perfect spheres assuming that void space volume is constant at 40%.
Figure 12A:
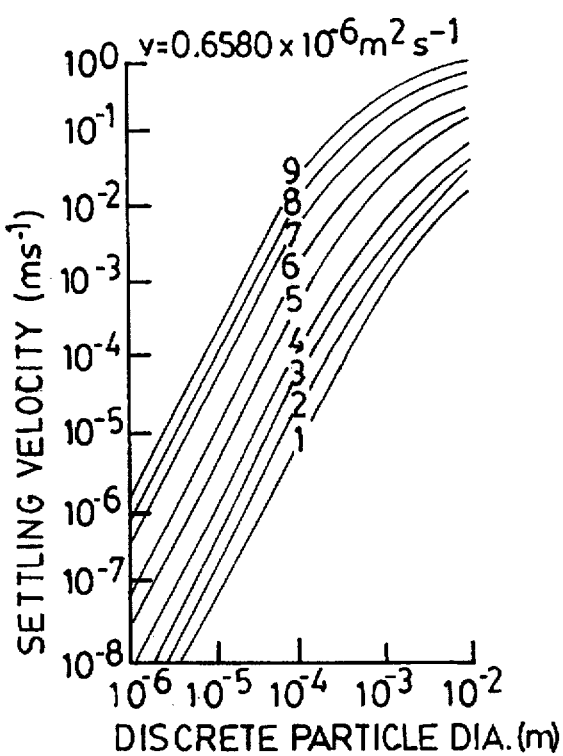
FIGS. 12A–12H are nomographs showing the settling velocities and rise velocities of particles of various sizes and specific gravities at various temperatures in water.
Figure 12B:
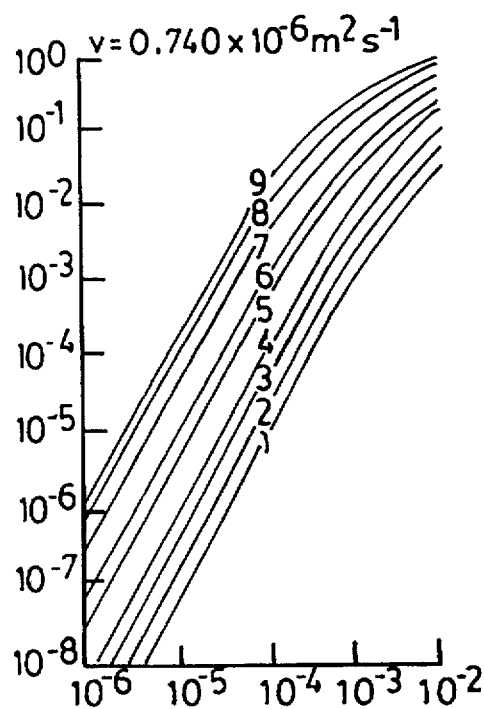
Figure 12C:
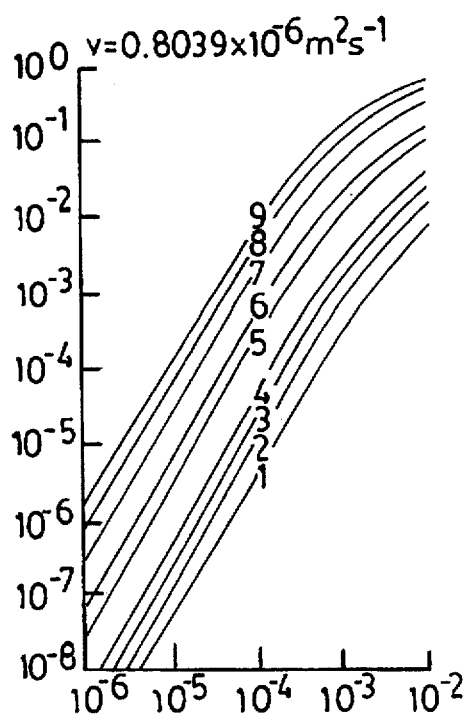
Figure 12D:
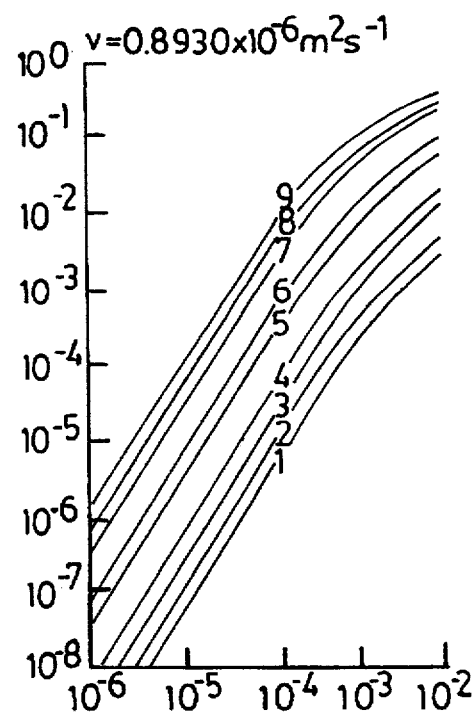
Figure 12E:
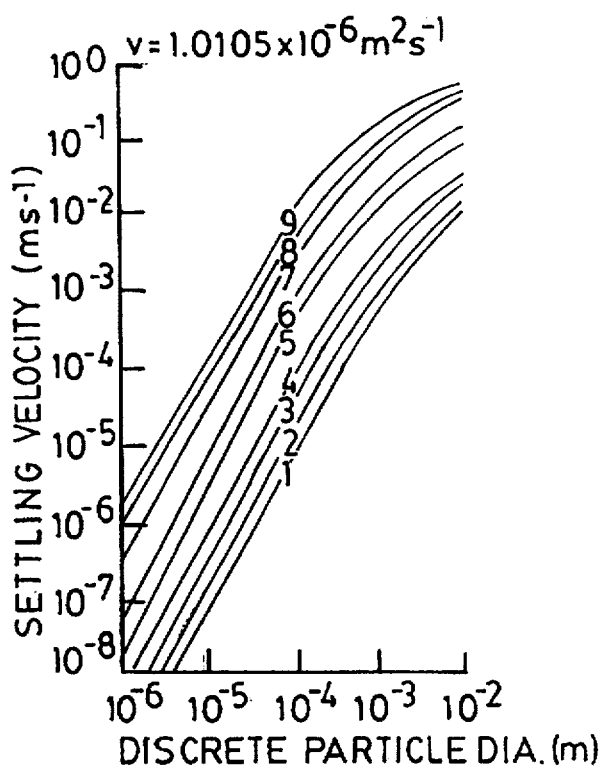
Figure 12F:
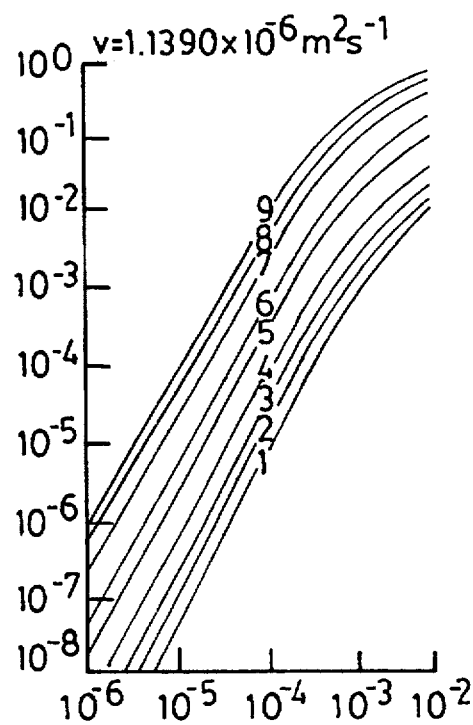
Figure 12G:
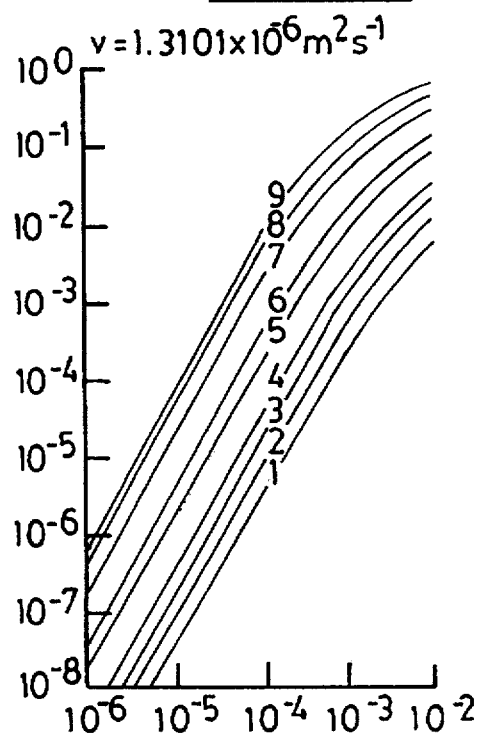
Figure 12H:
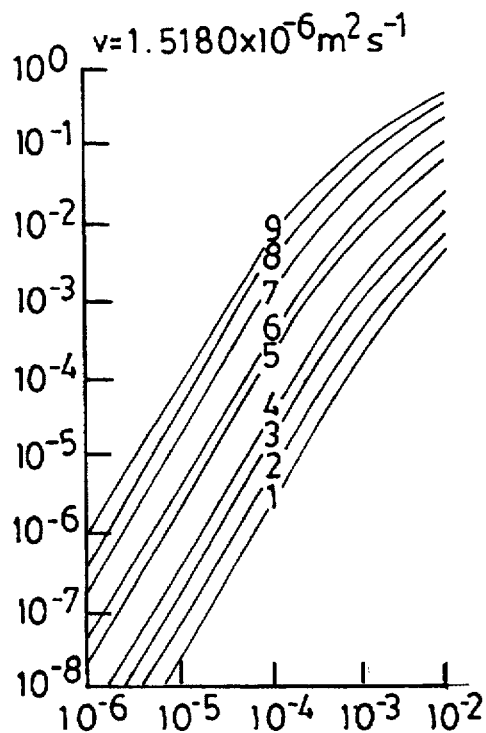

The exceptionally large surface area created by the use of small particles for biofilm attachment is illustrated in FIG. 11. If it were possible to manage particles as small as 10 $\mu$ in a static bed, 10 $\mu$ particles would provide over 50 acres of surface area for microbial attachment per cubic meter of reactor. Because microbial films are thicker than 10 $\mu$ in many cases, this does not represent a practical particle size for many applications, but it does represent the theoretical ideal particle. Even with particles as large as 1 mm, the interfacial surface area is approximately 1 acre/m$^3$ of reactor. In viewing the unit volume interfacial surface area shown in FIG. 11, it is important to keep in mind that the degree of expansion utilized in the reactor will decrease the interfacial surface area per unit volume.

Figure 13:
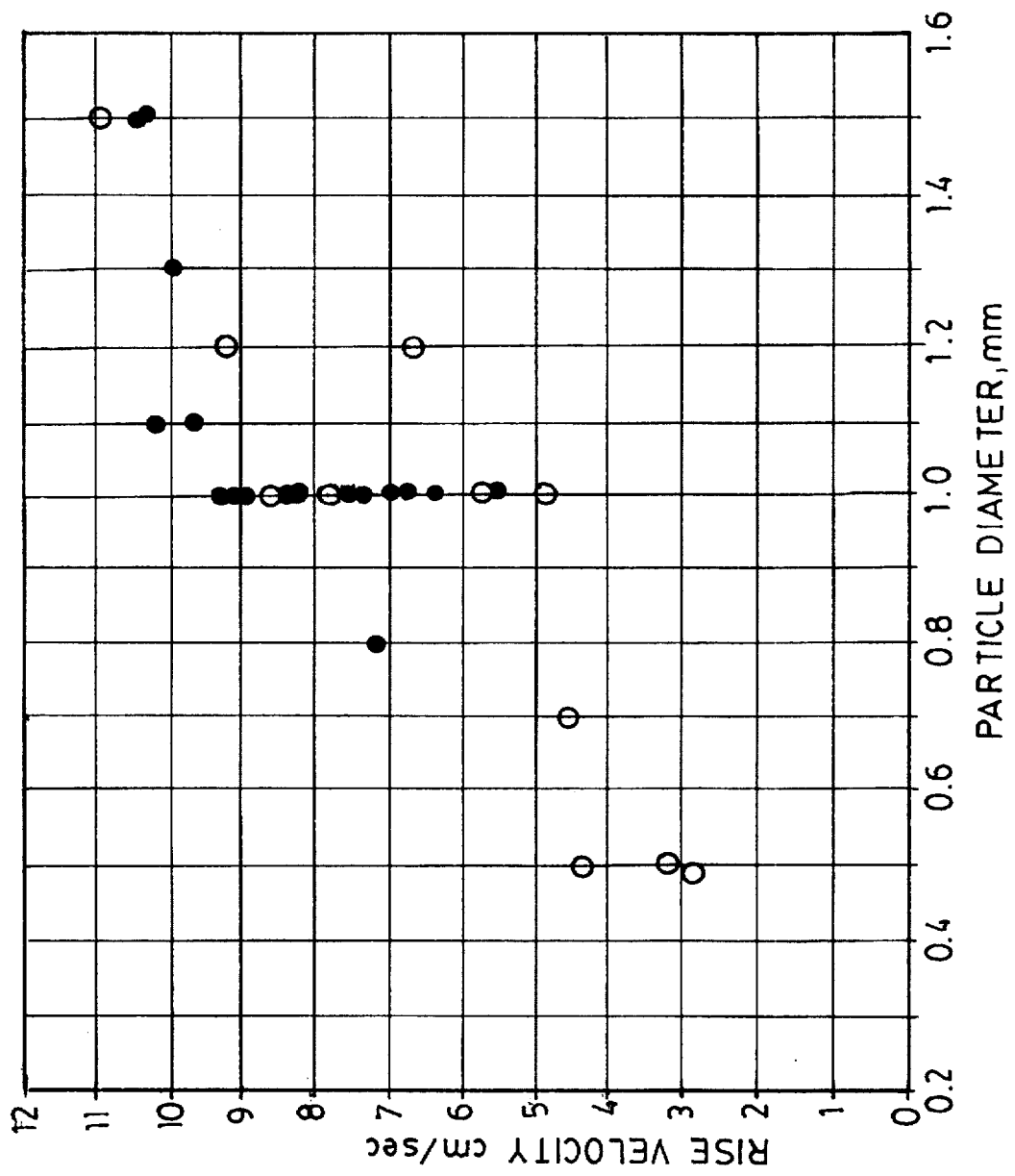
FIG. 13 is a graph of the rise velocities of individual particles in water at 10° C. in a small diameter tube (5.11 cm ID) with air bubbles (open circles) and STYROFOAM™ particles (closed circles).
Figure 14:
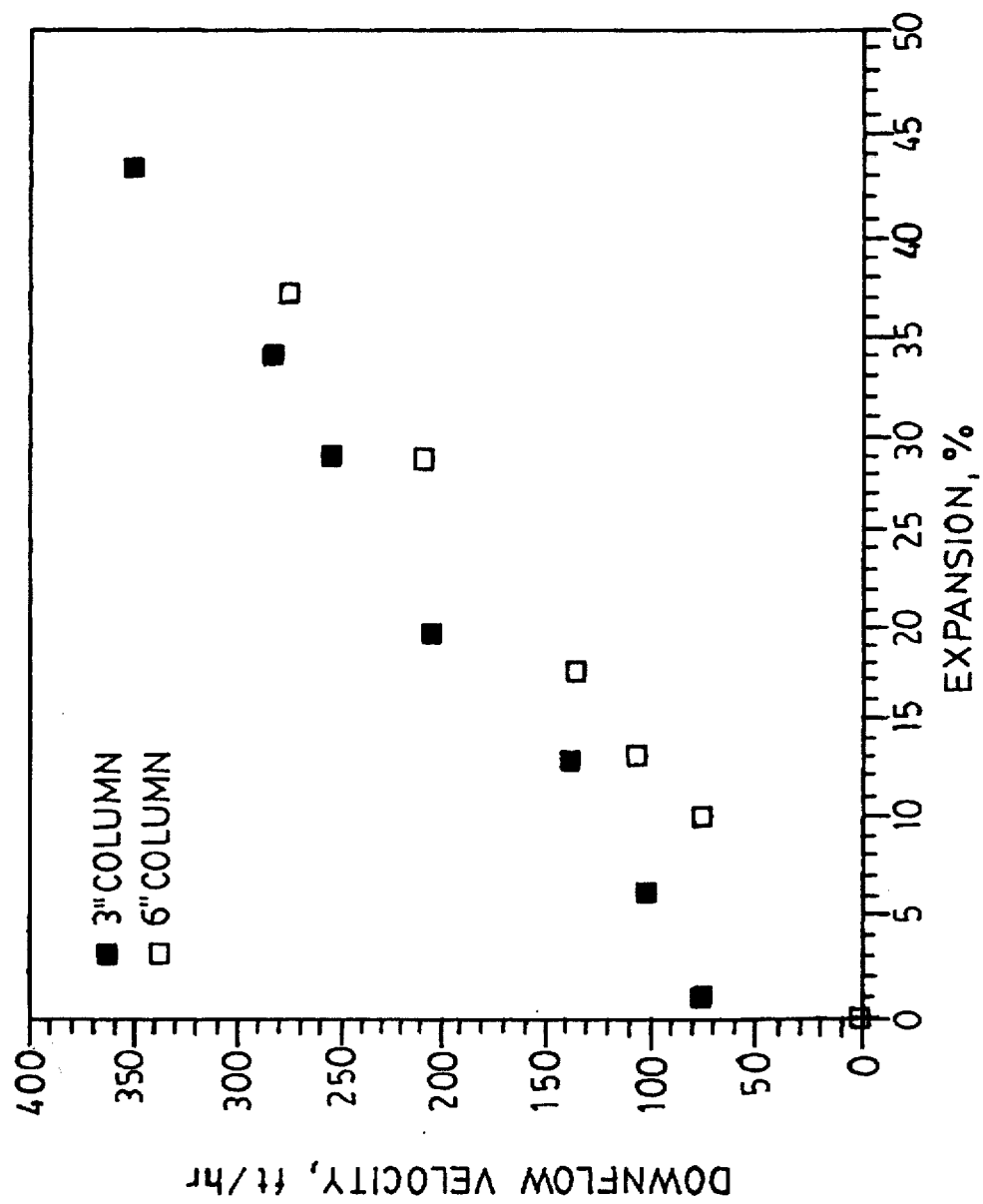
FIG. 14 is a graph depicting the relationship of downflow velocity (empty bed calculation) and bed expansion with 1 mm diameter STYROFOAM™ particles in a floating expanded bed.
Figure 15:
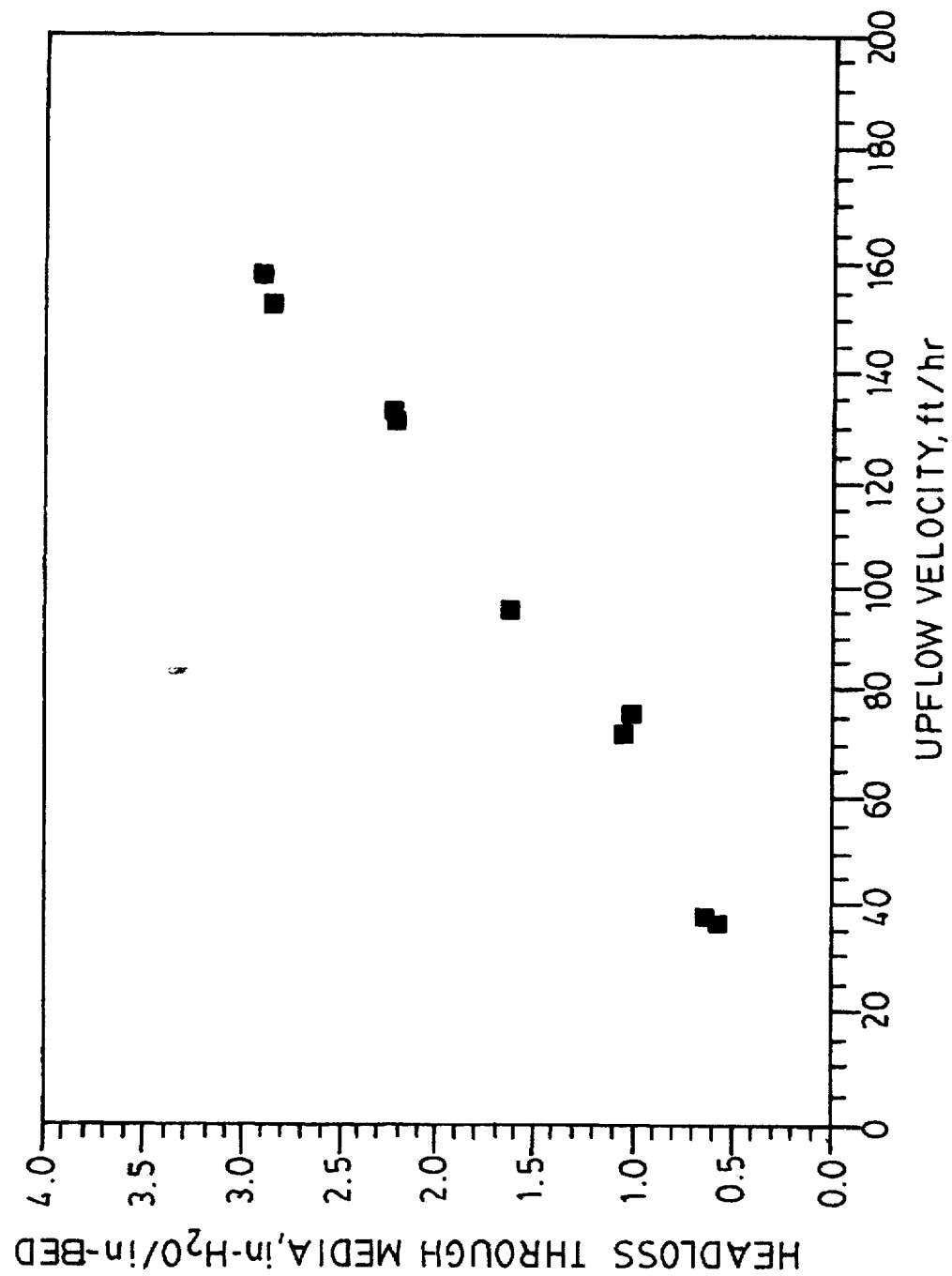
FIG. 15 is a graph relating headloss to upflow velocity when operating a floating expanded bed in an upflow mode (bed volume in static form) with 1 mm diameter clean (new) STYROFOAM™ particles.

The rise or settling velocity characteristic of particles is dependent upon viscosity of the dispersing fluid, temperature, and particle density. A summary of the relationship of different temperatures, diameters of particles and their settling velocities, as disclosed in Bhargava, et al., "An Integrated Expression For Settling Velocity of Particles in Water," *Water Research* 26:1005–1008 (1992) ("Bhargava"), which is hereby incorporated by reference, is reproduced in Table 4. Sand-sized particles at 35° C. with a diameter of 10 μ have a settling velocity of only 1 ft/hour, and with increased viscosity this decreases slightly. Practical limits on the desired hydraulic retention times at these slow settling rates make these particles unacceptable for upflow applications because they are difficult to remove by separation. Optimum-size particles for higher biomass density reactors with large interfacial surface areas would have diameters varying between 20 and 200μ. Experiments with floating particles (1 mm STYROFOAM™ beads) indicate that the empirical relationships of viscosity and friction loss result in rise velocities similar to the settling velocities shown in Table 4 for a particle density of 1.5. These empirical rise velocities will be utilized to illustrate the potential of floating bed reactors. For a range of velocities describing the varying temperature effects, see FIGS. 12A–12H, which are reproduced from Bhargava, which is hereby incorporated by reference.

approximately $2 per cubic foot and has a particle size ranging from 0.1 mm to nearly 2 mm with 90% of the particles being around 1 mm±approximately 10%. Rise velocity experiments with air bubbles and STYROFOAM™ beads are shown in FIG. 13. Additional experiments to illustrate the relationship of downflow headloss and bed expansion with these particles are shown in FIGS. 14 and 15, and headlosses in a downflow mode are summarized in Table 5. The average rise velocity of a 1 mm STYROFOAM™ particle is approximately 8 cm/sec. The relationship of expansion through empty bed velocity and the percent of the rise velocity required is shown in Table 6. At 10% of the rise velocity at 100° C. results in approximately 10% bed expansion. At a downflow velocity equal to 50% of rise velocity of the particles, the bed remains in a relatively static mode but is approximately 100% expanded, that is, 50% of the surface area available in a static bed is achieved by an expanded floating bed when operating at 50% of its partial rise velocity. Experimental definition of the 1 mm STYROFOAM™ particle indicates that they are highly stable at exceptionally high velocities and that a nonturbulent expanded bed can occur at greater than 200% bed expansion. This would indicate that the downflow of a bioreactor with a depth of approximately 3 m would have hydraulic retention times as short as several minutes, and

TABLE 4

Summary of settling velocities for varying size particles, densities, and temperatures (from Bhargava)

| Particle Diameter μ | 30° C., ρ = 2.65 m/sec | 10° C., ρ = 2.65 m/sec | 30° C., ρ = 1.50 m/sec | 30° C., ρ = 1.01 m/sec | 10° C., ρ = 1.01 m/sec |
|---|---|---|---|---|---|
| 1 | $1.6 \times 10^{-6}$ | $8 \times 10^{-7}$ | $6 \times 10^{-7}$ | $6 \times 10^{-9}$ | — |
| 10 | $1 \times 10^{-4}$ | $8.5 \times 10^{-5}$ | $3 \times 10^{-5}$ | $7 \times 10^{-7}$ | $5 \times 10^{-7}$ |
| 50 | $9 \times 10^{-4}$ | $9.4 \times 10^{-4}$ | $2 \times 10^{-4}$ | $8 \times 10^{-6}$ | $5 \times 10^{-6}$ |
| 100 | $8 \times 10^{-3}$ | $9 \times 10^{-3}$ | $2 \times 10^{-3}$ | $8 \times 10^{-5}$ | $6 \times 10^{-5}$ |
| 200 | $2 \times 10^{-2}$ | $2 \times 10^{-2}$ | $8 \times 10^{-3}$ | $2 \times 10^{-4}$ | $1.5 \times 10^{-4}$ |
| 1000 | $1.4 \times 10^{-1}$ | $2 \times 10^{-1}$ | $8 \times 10^{-2}$ | $5 \times 10^{-3}$ | $5 \times 10^{-3}$ |
| 2000 | $2 \times 10^{-1}$ | $4 \times 10^{-1}$ | $1 \times 10^{-1}$ | $8 \times 10^{-3}$ | $8 \times 10^{-3}$ |
| 5000 | $4 \times 10^{-1}$ | $6 \times 10^{-1}$ | $2 \times 10^{-1}$ | $2 \times 10^{-2}$ | $1.5 \times 10^{-2}$ |
| 10000 | $8 \times 10^{-1}$ | $8 \times 10^{-1}$ | $5 \times 10^{-1}$ | $7 \times 10^{-2}$ | $5 \times 10^{-2}$ |

Figure 16:
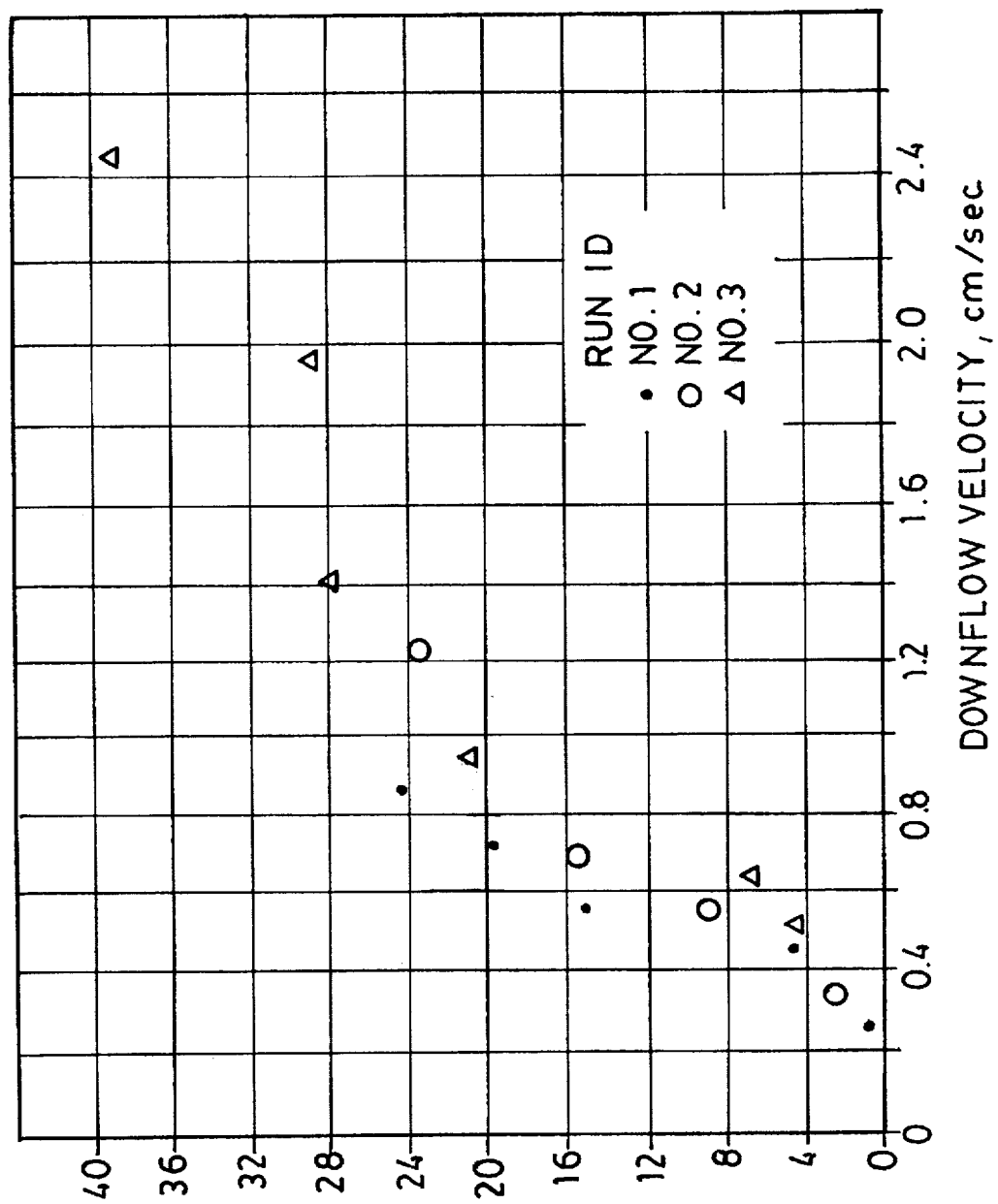
FIG. 16 is a graph relating downflow rate to bed expansion with a STYROFOAM™ medium having nominal 1 mm diameter in water at 11° C. for smaller bed expansions.
Figure 17:
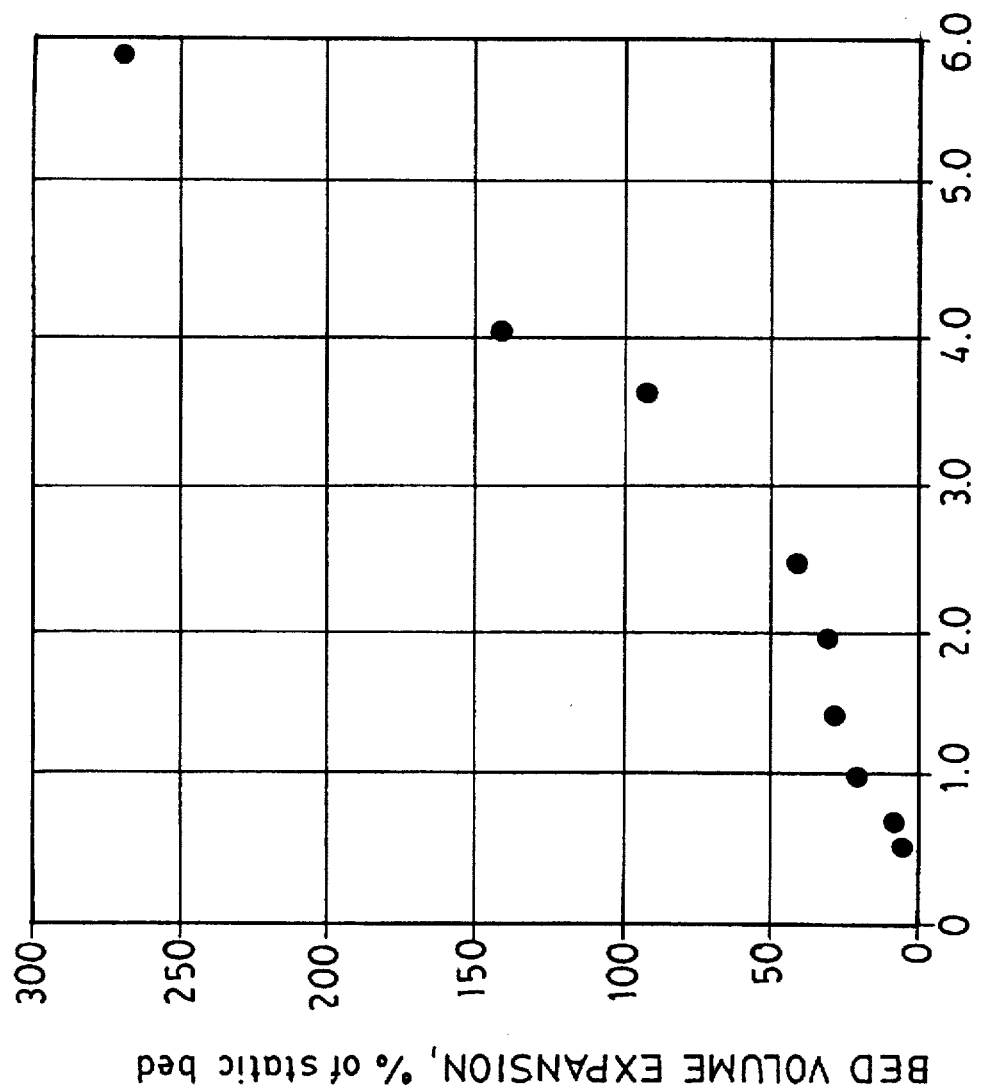
FIG. 17 is a graph of bed volume increase relative to static volume as a function of downflow velocity for 1 mm STYROFOAM™ particles for larger bed expansions.

There are numerous materials available with densities less than 1. However, one of the lowest-cost materials is a STYROFOAM™ bead marketed for fabrication of various STYROFOAM™ products. This bead can be obtained for this high velocity would still result in conditions favorable for biofilm development and maintenance. Further, information on the expansion achieved by various downflow velocities are given in FIGS. 16 and 17.

TABLE 5

Summary of headloss measurements with floating bed particles one mm diameter STYROFOAM ™ in a 6-inch diameter column. Tests with a 54-inch diameter tap 46.5-inch deep unit with similar particles and an established biofilm recorded 0.4 m/in headloss
SA = 28.27433 sq in
82.4147 sq cm

| CYCLE | MEDIA DEPTH (in) | VOLUME (l) | TIME SEC | HEAD LOSS (in) | HEAD LOSS (in/in) | FLOW RATE (l/min) | VELOCIT (ft/hr) | EXPANSION (%) |
|---|---|---|---|---|---|---|---|---|
| 1 | 7.20 | 0.00 | 0.00 | 0.00 | 0.00 | 0.00 | 0.00 | 0.00 |
| 2 | 8.00 | 5.11 | 45.00 | 3.75 | 0.47 | 6.81 | 73.45 | 10.00 |
| 3 | 8.30 | 7.29 | 45.00 | 3.80 | 0.46 | 9.72 | 104.89 | 13.25 |
| 4 | 8.75 | 9.35 | 45.00 | 4.00 | 0.46 | 12.46 | 134.46 | 17.71 |
| 5 | 10.13 | 9.66 | 30.00 | 4.00 | 0.40 | 19.32 | 208.45 | 28.89 |
| 6 | 11.50 | 12.65 | 30.00 | 4.00 | 0.35 | 25.30 | 272.98 | 37.39 |

TABLE 6

Relationship between downflow velocity and bed expansion with one mm diameter STYROFOAM ™ beads at 11° C.

| Observed Expansion, % Static Volume | Empty Bed Downflow Velocity cm/sec | Downflow Velocity, % of Avg. Particle Rise Velocity |
|---|---|---|
| 10 | 0.8 | 10 |
| 20 | 1.2 | 15 |
| 50 | 2.8 | 35 |
| 100 | 3.8 | 50 |
| 200 | 4.6 | 60 |

The quantity of biofilm that accumulates on the surface, its depth of accumulation, and density are dependent on a large number of environmental factors. However, there are a certain number of limitations that can be used to define requirements of a particle in a biofilm reactor. As has been reported for many different microbial applications, aerobic films almost always have a density of 30 g VS/l$_f$. As indicated earlier in Table 2, the density of anaerobic films varies over a wide range. If one assumes that a general relationship for the biofilm in terms of design requirements, such as solid retention time, the relatively constant anaerobic and aerobic film accumulation surfaces can be used to specify the quantity of interfacial surface area required. Estimation of the interfacial surface area requirements for a biofilm reactor given a limited number of parameters is provided in Table 7. Data in this table indicate that for aerobic reactions treating wastewater at ambient temperatures with a 60 minute hydraulic retention time will require 6,000 to 12,000 m² per m³ of reactor, and anaerobic reactors would require a higher surface area of around 18,000 m² per m³ of surface area. Data relating particle diameter to surface area show that particles with 1 mm diameter or slightly less are useful for aerobic applications, and particles with 100 to 200 µ would be the best size of particles for anaerobic reactions. The question of whether these particles could be managed efficiently and be separated from the flow dictates the kind of process that would utilize various density particles. The acceptability of the particles is defined by their settling or rise velocity.

The data presented in Table 7, indicating range of interfacial surface area per unit volume required for aerobic and anaerobic biofilm applications, significantly reduce the number of variables that must be specified in designing a film reactor.

TABLE 7

Relationship between required bioreactor surface area, interfacial surface area loading and microbial growths requirements (solids retention time and cellular yield) for waste management applications

| | Application | |
|---|---|---|
| | Aerobic | Anaerobic |
| Microbial Growth Assumption SRT, days | 20 | 100 |
| Net Yield, g VS/g substrate | 0.25 to 0.5 | 0.15 |
| Substrate Interfacial Area Loading Rate, g substrate/m²$_{film}$-d | 0.5 to 1.0 | 0.33 |
| Required Interfacial Surface Area @ BOD = 250 mg/l, HRT = 1 hr m²/m³ | 6000 to 12,000 | 18,000 |

Three examples serve to further illustrate the approach to specifying particles and floating bioreactor requirements.

Anaerobic sewage treatment is demonstrated with a floating STYROFOAM™ bed. Another example relates to aquaculture. The third example illustrates chemical production with microbial generation of ethanol.

The overall results of these three examples and the assumptions that were used therein are shown in Tables 8, 9, and 10. These tables relate the range of particle sizes to the design relationship. In the sewage example, if the object is to obtain as small a reactor as possible, then, to meet the objectives of the design, there are about three STYROFOAM™ bead particle sizes that would be acceptable. These range from 200 µ to 1 mm. The smaller particle achieves the desired biomass and therefore efficiency at 1.5 hour retention time, whereas the larger 1 mm particle requires an 8-hour retention time or longer. Even more important, rise velocities at shorter retention times are significantly greater than downflow velocities; thus, the reactor is a feasible design using small particles, and required expansion and suspended solids management can be achieved by recycling effluent, if desired. Estimated biomass concentrations for the anaerobic system with 200 µ particles indicate that the reactor biomass concentration would have approximately 45 g VS/l$_r$. Aerobic film with particles this size would have approximately 27 g/m².

TABLE 8

Anaerobic sewage treatment example

Problem description and assumptions:

Domestic sewage generated from 10,000 people
Flow = 1,000,000 gal/d, 3800 m³/d
Organic matter = 250 mg/l BOD$_5$, 950 kg BOD$_5$/d
Require ≦30 mg/l effluent BOD$_5$
Temperature, winter minimum = 10° C.
Biofilm thickness = 12 × 10⁻⁶ m
Biofilm density = 300 g VS/l$_f$
Biofilm design interfacial loading rate = 0.216 g BOD/m²-d at 90+% removal eff.
Required surface area = 4.4 × 10⁶ m²
Microbial yield = 0.12 g VS/g COD removed

| Particle Size, m | Specific surface, m²/m³ | Required Vol, m³ | Area*, m² | Downflow Velocity, m/min | Design HRT, days | Particle Rise Velocity, m/min |
|---|---|---|---|---|---|---|
| 0.02 | 180 | 24,400 | 12,200 | 0.00022 | 6.42 | 54 |
| 0.01 | 360 | 12,200 | 6,100 | 0.00043 | 3.20 | 36 |
| 0.002 | 1800 | 2400 | 1220 | 0.0022 | 0.64 | 6 |
| 0.001 | 3600 | 1220 | 610 | 0.0043 | 0.32 | 4.3 |
| (0.0005) | 7200 | 611 | 305 | 0.0086 | 0.16 | 0.6 |
| 0.0002 | 18,000 | 244 | 122 | 0.022 | 0.064 | 0.36** |
| 0.0001 | 36,000 | 122 | 61 | 0.043 | 0.032 | 0.12 |
| 0.00002 | 180,000 | 24 | 12 | 0.22 | 0.006 | 0.004 |
| 0.00001 | 360,000 | 12 | 6 | 0.43 | 0.0032 | 0.001 |

*Assumed depth = 2 m
** @ 5 g VS/m², VS = 90 g/l okay

Biomass surface area density = 5 g VS/m², with 200 µ particle φ, reactor solids = 90 g VS/l, acceptable level for anaerobic fills.

TABLE 9

Aquaculture Example

Reactor sie for given fish production tank to achieve complete biological nitrification Fish tank size = 20 ft $\phi$ × 4 ft deep
Vol. = 314 × 4 = 1256 ft$^3$ (4.8 m$^3$)
Stocking density = 5 lb/ft$^3$, or 6280 lb fish
Production = 6280 lb, twice per year
Feed rate @ 3% weight = 190 lb/d
$NH_3$—H gen. rate @ 3% of feed rate = 4.5 lb/d or
$NH_3$—H accumulation rate = 73 mg/l-d
Required flow rate to maintain 0.5 mg/l $NH_3$—H or
less of 2600 g/d (assumes 100% conversion per pass)
= 950 gal/min
(1.4 MGD), (3.6 m$^3$/min)
Net bioreactor design loading rate = 0.1 g $NH_3$—N/m$^2$-d
Required Surface Area = 26,000 m$^2$

| Particle Size, $\phi$ m | | Specific Surface Area m$^2$/m$^3$ reactor | Required Reactor Volume, m$^3$ | Resulting Hydraulic Retention Time, minutes | Area | Downflow Velocity, m/min | System Requirements Volume as % Fish Growing Tank | STYROFOAM ™ Particle Rise Vol., m/min |
|---|---|---|---|---|---|---|---|---|
| 0.02 | 2 cm | 180 | 144 | 72 | 40 | 0.005 | 3000 | 54 |
| 0.01 | 1 cm | 360 | 72 | 36 | 20 | 0.001 | 1500 | 36 |
| 0.002 | 2 mm | 1800 | 14 | 7.2 | 4 | 0.5 | 300 | 6 |
| 0.001 | 1 mm | 3600 | 7 | 3.6 | 2 | 0.1 | 150* | 4.8 |
| 0.0002 | 200µ | 18000 | 1.4 | 0.72 | 0.4 | 5 | 30* | 0.36 |
| 0.0001 | 100µ | 36,000 | 0.7 | 0.36 | 0.2 | 3 | 15 | 0.12 |
| 0.00002 | 20µ | 180,000 | 0.14 | 0.072 | 0.04 | 50 | 3 | 0.004 |
| 0.00001 | 10µ | 360,000 | 0.07 | 0.036 | 0.02 | 30 | 1.5 | 0.001 |

Treatment system assumed to be 2 m deep.
Volumetric loading rates with 1 mm particle.

TABLE 10

Ethanol production using attached *Zymononas mobilis*

Daily production Rate = 10,000 gal = 65,000 lb = 30 × 10$^3$ kg
Sugar feed rate = 100 g glucose/l, converts to 30 g ethanol/l or
Volume flow = (30 × 10$^6$ g/d)/(100 g/l) = 30 × 10$^4$ l/d or 300 m$^3$/d
30% conversion rate
Need (30 × 10$^3$ kg/d)/0.3 = 100 × 10$^3$ kg/d sugar
Biomass = 60 g VS/l unexpanded bed
Particle size = 300µ
Film thickness = 170µ
Density = 30 g VS/l$_f$
VOLR = 200 g/l-hi
Yield = 0.4 g VS/g sugar
SOLR = 400 g glucose/m$^2$-d
Total required surface area = 75,000 m$^2$

| Particle size | Surface Area m2/m$^3$ | Required Volume m$^3$ | Required Area m$^2$ | HRT d | Downflow Vel. m/d |
|---|---|---|---|---|---|
| 0.02 | 180 | 416 | 139 | 1.4 | 2.15 |
| 0.01 | 360 | 208 | 69 | 0.69 | 4.3 |
| 0.002 | 1800 | 42 | 14 | 0.14 | 21.4 |
| 0.001 | 3600 | 21 | 7 | 0.07 | 43 |
| 0.0002 | 18,000 | 4.2 | 1.4 | 0.014 | 215 |
| 0.0001 | 36,000 | —* | — | — | — |
| 0.00002 | 180,000 | — | — | — | — |
| 0.00001 | 360,000 | — | — | — | — |

*Particles too small to accommodate a thick aerobic biofilm.
Depth = 3 m

The examples show that anaerobic reactors can efficiently treat sewage and can convert the organic matter to natural gas. However, the critical parameter is that the biofilm must be maintained in the reactor for exceptionally long periods of time for wintertime conditions. The solid retention time must be greater than 300 days. If the yield is less 0.15 g VS/g BOD, then the solid retention time in this application with particles of 100 to 200 µ would be around 300 days for the example shown in Table 8, meeting the exceptionally long solid retention time requirement for this unique application of biofilm reactors. Note that use of a buoyant particle to satisfy this design condition offers a wide range of possibilities with shallow horizontal flow being possible because of low rise velocities.

Using buoyant media in the processes of the present invention presents several advantages. Buoyant-medium reactors can be used for bioconversion and suspended solids separation and accumulation without problems with clogging. Buoyant media can be utilized as static beds and intermittently expanded for biofilm management. Biofilm management can be accomplished using mechanical, liquid, or gaseous flows. Suspended solids filtration at high flow rates can be achieved because of the creation of microlaminar zones on the particles. Thus hydraulic retention times of several minutes would be expected to achieve significant suspended solids separation. Buoyant media introduce the possibility of an exceptionally high interfacial surface area bed as a static bed without bed expansion, thus enabling a maximum surface area to be achieved with minimum clogging potential.

Buoyant media enable a plug flow large interfacial surface area reactor to be utilized in a horizontal flow mode. The buoyant-media reactor eliminates flow redistribution and bed management problems. The easiest form of flow distribution is to have suspended weirs over the medium. However, for small reactors, no distribution is required, and only an exit pipe is necessary.

Counter-current flow would achieve maximum filtration of suspended solids because of low weight of the bed and low headlosses that can be achieved with materials such as small STYROFOAM™ particles. The use of light, buoyant particles and their movement into and out of the bed for bed set-up and maintenance and in transportation allows lower construction costs and techniques to be used for reactor design (such as the use of flexible-liner reactors). The light, buoyant particles and slow hydraulic flows utilized in many of the applications are highly compatible with the fragile biofilm so that shearing and film management are much more compatible than upflow fluidized bed designs that use heavier, more dense, and hard particles.

Flexible flow distribution combined with recycle enables many different combinations of bioreactor and filtration to be considered. The surface area, recycle ratio, and rise velocity compared to the higher-density settling particles enables a larger interfacial surface area to be used at velocities common in waste applications. Floating particles also make separation of horizontal flows and vertical flows easier, so that the headloss through the bed, suspended solids management, and biofilm management can be optimized in one reactor.

Microbial kinetics and biofilm characteristics can be matched with particle management requirements to obtain optimum efficiencies and conversion rates. Assuming a viable biofilm concentration of 3 g VS/m$^2$, estimates of required particle size to achieve practical reactor biomass concentrations for optimum particle management can be made. Aerobic reactors will target 15 to 30 g VS/l$_r$ and anaerobic reactors will target 30 to 200 g VS/l$_r$.

In cases in which required surface area results in downflow velocities that exceed the rise velocity of particles, two options are available for particle management: horizontal flow-through the bed may be utilized with downward expansion controlled by recycle or diversion of part of inflow. Mechanical expansion with augers or other physical components can also be used.

Recycle flow may be used to control headloss through the bed, bed expansion, suspended solids accumulation in the bed, and biofilm accumulation.

When combined bioconversion and suspended solids separation is desired, the floating bed can be operated to achieve suspended solids separation when inflow suspended solids varies from less than 100 mg/l to greater than 10,000 mg/l of sludge-like suspended solids. Upflow directions of the flow through the buoyant media can be used with a static, unexpanded bed to remove suspended solids. Intermittent backflow flushing could be used to remove entrapped solids. Also physical mechanisms moving in direction opposite to flow, with augers or other mechanical devices that actual move the media counter-current to flow direction, would be useful. Counter-current liquid flow using recycle of a treated effluent can be used to create velocities in the downflow direction to enhance suspended solids separation from the flow from a lower velocity upflow effluent that passes through a static or an expanded filter section or clarifier.

Suspended solids separation can use similar optional designs and processes as the bioconversion system. For example, the process can be operated in an expanded downflow mode (static or expanded), in an upflow mode (static or expanded), or in a counter-current flow mode.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A process for chemical modification of a reactant by microbes, said process comprising:

providing a particulate material dispersed in a dispersing fluid wherein the particulate material has a specific gravity less than the specific gravity of the dispersing fluid and wherein the particulate material comprises a polymeric carrier and microbes attached to the carrier; and establishing a flow of the reactant through the particulate material, wherein the flow is effective to contact the reactant with the microbes for a time sufficient to chemically modify the reactant, provided that, when said process is carried out under conditions conducive to anaerobic microbe viability, the particulate material has an operating interfacial surface area of from about 2,000 to about 240,000 square meters per cubic meter of particulate material volume and provided that, when said process is carried out under conditions conducive to aerobic microbe viability, the particulate material has an operating interfacial surface area of from about 1,000 to about 30,000 square meters per cubic meter of reactor volume.

2. A process according to claim 1, wherein the reactant is dispersed in water.

3. A process according to claim 1, wherein the dispersing fluid is water.

4. A process according to claim 1, wherein the flow has a downward component effective to form an expanded bed of the particulate material in the dispersing fluid.

5. A process according to claim 1, wherein said process is carried out under conditions conductive to anaerobic microbe viability.

6. A process according to claim 5, wherein the particulate material has an operating interfacial surface area from about 4,000 to about 24,000 square meters per cubic meter of reactor volume.

7. A process according to claim 5, wherein the particulate material is substantially spherical and has an average diameter of from about 0.02 mm to about 2 mm.

8. A process according to claim 5, wherein the particulate material is substantially spherical and has an average diameter of from about 0.02 mm to about 1.2 mm.

9. A process according to claim 5, wherein the microbes attached to the carrier form a film on the carrier, the film having a thickness of from about 5µ to about 100µ.

10. A process according to claim 1, wherein said process is carried out under conditions conductive to aerobic microbe viability.

11. A process according to claim 10, wherein the particulate material has an operating interfacial surface area from about 2,000 to about 6,000 square meters per cubic meter of reactor volume.

12. A process according to claim 10, wherein the particulate material is substantially spherical and has an average diameter of from about 0.2 mm to about 2 mm.

13. A process according to claim 10, wherein the particulate material is substantially spherical and has an average diameter of from about 0.3 mm to about 1 mm.

14. A process according to claim 10, wherein the microbes attached to the carrier form a film on the carrier, the film having a thickness of from about 50µ to about 300µ.

15. A process according to claim 1, wherein the carrier comprises a foamed plastic having a density of from about 0.02 g/mL to about 0.95 g/mL.

16. A process according to claim 15, wherein the foamed plastic is foamed polystyrene.

17. A process according to claim 1, wherein the reactant is ammonia, the chemical modification is nitrification, and the dispersing fluid contains an amount of oxygen sufficient to effect nitrification of the ammonia.

18. A process according to claim 1, wherein the reactant is nitrate and the chemical modification is denitrification.

19. A process according to claim 1, wherein the reactant is a sugar or a mixture of sugars and the chemical modification results from fermentation.

20. A process according to claim 19, wherein the sugar is glucose.

21. A process according to claim 1, wherein the reactant is organic matter having a biological oxygen demand and the chemical modification results from anaerobic fermentation.

22. A process according to claim 1, further comprising:
   recirculating a portion of the flow of the reactant from a downstream flow region to an upstream flow region in the particulate material.

23. A process according to claim 1, wherein the flow has both horizontal and vertical components.

* * * * *